(12) United States Patent
Tomkinson et al.

(10) Patent No.: US 7,951,833 B2
(45) Date of Patent: *May 31, 2011

(54) CRYSTALLINE FORMS OF 4-[4-(2-ADAMANTYLCARBAMOYL)-5-TERT-BUTYL-PYRAZOL-1-YL]BENZOIC ACID 471

(75) Inventors: Gary Peter Tomkinson, Macclesfield (GB); Martin John Packer, Macclesfield (GB); James Stewart Scott, Macclesfield (GB); Paul Robert Owen Whittamore, Macclesfield (GB); Andrew Stocker, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/364,949

(22) Filed: Feb. 3, 2009

(65) Prior Publication Data

US 2009/0221660 A1 Sep. 3, 2009

Related U.S. Application Data

(60) Provisional application No. 61/082,293, filed on Jul. 21, 2008.

(30) Foreign Application Priority Data

Feb. 4, 2008 (PK) ..................... 108/2008
Feb. 11, 2008 (WO) ................ PCT/GB2008/000454

(51) Int. Cl.
*A61K 31/415* (2006.01)
*C07D 231/12* (2006.01)

(52) U.S. Cl. ..................... 514/406; 548/374.1

(58) Field of Classification Search .................. None
See application file for complete search history.

(56) References Cited

U.S. PATENT DOCUMENTS

| | | |
|---|---|---|
| 2006/0223852 A1 | 10/2006 | Gillespie et al. |
| 2008/0269288 A1 | 10/2008 | McCoull et al. |
| 2009/0221663 A1 | 9/2009 | Packer et al. |
| 2009/0264401 A1 | 10/2009 | Gill et al. |
| 2009/0306075 A1 | 12/2009 | McCoull et al. |
| 2009/0312372 A1 | 12/2009 | McCoull et al. |
| 2010/0022589 A1 | 1/2010 | McCoull et al. |

FOREIGN PATENT DOCUMENTS

| | | |
|---|---|---|
| EP | 1889842 | 2/2008 |
| EP | 1894919 | 3/2008 |
| WO | WO 2004/089470 | 10/2004 |
| WO | WO 2005/016877 | 2/2005 |
| WO | WO 2005/108359 | 11/2005 |
| WO | WO 2006/048750 | 5/2006 |
| WO | WO 2006/106054 | 10/2006 |
| WO | WO 2006/113261 | 10/2006 |
| WO | WO 2006/132197 | 12/2006 |
| WO | WO 2006/132436 | 12/2006 |
| WO | WO 2007/052843 | 5/2007 |
| WO | WO 2007/058346 | 5/2007 |
| WO | WO 2008/012532 | 1/2008 |
| WO | WO 2008/053194 | 5/2008 |
| WO | WO 2008/099145 | * 8/2008 |
| WO | WO 2008/142986 | 11/2008 |
| WO | WO 2009/010416 | 1/2009 |

OTHER PUBLICATIONS

Brittain et al. "Polymorphism in Pharmaceutical Dosage Forms." Polymorphism in Pharmaceutical Solids XX (Jan. 1999), relevant pages attached.*
Morissette et al. Advanced Drug Delivery Reviews 2004, 56, 275-300.*
Vippagunta et al. Advanced Drug Delivery Reviews 2001, 48, 3-26, abstract.*
Blake et al. "Discovery of 3,3-dimethyl-azetidin-2-ones as potent and selective inhibitors of 11β-HSD1" Gordon Research Conference on Medicinal Chemistry, Colby-Sawyer College, New London, NH, USA (Aug. 2007).
Boyle "Recent advances in the discovery of 11b-HSD1 inhibitors" Current Opinion in Drug Discovery and Development 11:495-511 (2008).
deSchoolmeester et al. "An increase in obesity is associated with increased 11βHSD1 activity but not expression in mature human subcutaneous adipocytes" Association for the Study of Obesity (ASO) and Adipose Tissue Discussion Group, Institute of Child Health, London (Nov. 9, 2006).
Jean et al. "Inhibitors of 11â-HSD1: A Potential Treatment for the Metabolic Syndrome" Current Topics in Medicinal Chemistry 8(17): 1508-1523 (2008).
Mayers "11β-hydroxysteroid dehydrogenase type 1: a tale of (fat) mice to men" Abstract and Presentation, Obesity and its Treatment, Society for Medicines Research (Sep. 25, 2008).

* cited by examiner

*Primary Examiner* — Rebecca L Anderson
*Assistant Examiner* — Alicia L Otton
(74) *Attorney, Agent, or Firm* — Morgan, Lewis & Bockius LLP

(57) ABSTRACT

New crystalline forms of 4-[4-(2-adamantylcarbamoyl)-5-tert-butyl-pyrazol-1-yl]benzoic acid; their use in the inhibition of 11βHSD1, processes for making them and pharmaceutical compositions comprising them are also described.

7 Claims, 7 Drawing Sheets

CRYSTALLINE FORMS OF 4-[4-(2-ADAMANTYLCARBAMOYL)-5-TERT-BUTYL-PYRAZOL-1-YL]BENZOIC ACID 471

CROSS-REFERENCE TO RELATED APPLICATIONS

This application claims the benefit under 35 U.S.C. §119(a)-(d) of Application No. 108/2008 (PK) filed on 4 Feb. 2008; Application No. PCT/GB2008/000454 (WO) filed on 11 Feb. 2008 and 35 U.S.C. §119(e) of U.S. Application No. 61/082,293 filed on 21 Jul. 2008.

STATEMENT REGARDING FEDERALLY SPONSORED RESEARCH OR DEVELOPMENT

Not Applicable.

NAMES OF PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

This invention relates to novel crystalline forms of 4-[4-(2-adamantylcarbamoyl)-5-tert-butyl-pyrazol-1-yl]benzoic acid (the Agent). The Agent possesses human 11-β-hydroxysteroid dehydrogenase type 1 enzyme (11βHSD1) inhibitory activity and accordingly has value in the treatment of disease states including metabolic syndrome and are useful in methods of treatment of a warm-blooded animal, such as man. The invention also relates to processes for the manufacture of the crystalline forms of the Agent, to pharmaceutical compositions containing them and to their use in the manufacture of medicaments to inhibit 11βHSD1 in a warm-blooded animal, such as man.

The Agent is illustrated in Formula (I) hereinafter:

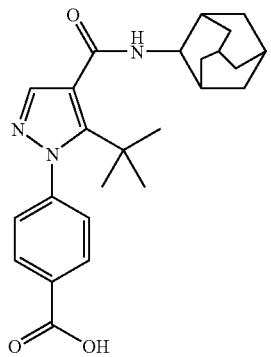

2. Description of Related Art

Glucocorticoids (cortisol in man, corticosterone in rodents) are counter regulatory hormones i.e. they oppose the actions of insulin (Dallman M F, Strack A M, Akana S F et al. 1993; Front Neuroendocrinol 14, 303-347). They regulate the expression of hepatic enzymes involved in gluconeogenesis and increase substrate supply by releasing glycerol from adipose tissue (increased lipolysis) and amino acids from muscle (decreased protein synthesis and increased protein degradation). Glucocorticoids are also important in the differentiation of pre-adipocytes into mature adipocytes which are able to store triglycerides (Bujalska I J et al. 1999; Endocrinology 140, 3188-3196). This may be critical in disease states where glucocorticoids induced by "stress" are associated with central obesity which itself is a strong risk factor for type 2 diabetes, hypertension and cardiovascular disease (Bjorntorp P & Rosmond R 2000; Int. J. Obesity 24, S80-S85).

It is now well established that glucocorticoid activity is controlled not simply by secretion of cortisol but also at the tissue level by intracellular interconversion of active cortisol and inactive cortisone by the 11-beta hydroxysteroid dehydrogenases, 11βHSD1 (which activates cortisone) and 11βHSD2 (which inactivates cortisol) (Sandeep T C & Walker B R 2001 Trends in Endocrinol & Metab. 12, 446-453). That this mechanism may be important in man was initially shown using carbenoxolone (an anti-ulcer drug which inhibits both 11βHSD1 and 2) treatment which (Walker B R et al. 1995; J. Clin. Endocrinol. Metab. 80, 3155-3159) leads to increased insulin sensitivity indicating that 11βHSD1 may well be regulating the effects of insulin by decreasing tissue levels of active glucocorticoids (Walker B R et al. 1995; J. Clin. Endocrinol. Metab. 80, 3155-3159).

Clinically, Cushing's syndrome is associated with cortisol excess which in turn is associated with glucose intolerance, central obesity (caused by stimulation of pre-adipocyte differentiation in this depot), dyslipidaemia and hypertension. Cushing's syndrome shows a number of clear parallels with metabolic syndrome. Even though the metabolic syndrome is not generally associated with excess circulating cortisol levels (Jessop D S et al. 2001; J. Clin. Endocrinol. Metab. 86, 4109-4114) abnormally high 11βHSD1 activity within tissues would be expected to have the same effect. In obese men it was shown that despite having similar or lower plasma cortisol levels than lean controls, 11βHSD1 activity in subcutaneous fat was greatly enhanced (Rask E et al. 2001; J. Clin. Endocrinol. Metab. 1418-1421). Furthermore, the central fat, associated with the metabolic syndrome expresses much higher levels of 11βHSD1 activity than subcutaneous fat (Bujalska I J et al. 1997; Lancet 349, 1210-1213). Thus there appears to be a link between glucocorticoids, 11βHSD1 and the metabolic syndrome.

11βHSD1 knock-out mice show attenuated glucocorticoid-induced activation of gluconeogenic enzymes in response to fasting and lower plasma glucose levels in response to stress or obesity (Kotelevtsev Y et al. 1997; Proc. Natl. Acad. Sci. USA 94, 14924-14929) indicating the utility of inhibition of 11βHSD1 in lowering of plasma glucose and hepatic glucose output in type 2 diabetes. Furthermore, these mice express an anti-atherogenic lipoprotein profile, having low triglycerides, increased HDL cholesterol and increased apo-lipoprotein AI levels. (Morton N M et al. 2001; J. Biol. Chem. 276, 41293-41300). This phenotype is due to an increased hepatic expression of enzymes of fat catabolism and PPARα. Again this indicates the utility of 11βHSD1 inhibition in treatment of the dyslipidaemia of the metabolic syndrome.

The most convincing demonstration of a link between the metabolic syndrome and 11βHSD1 comes from recent studies of transgenic mice over-expressing 11βHSD1 (Masuzaki H et al. 2001; Science 294, 2166-2170). When expressed under the control of an adipose specific promoter, 11βHSD1 transgenic mice have high adipose levels of corticosterone, central obesity, insulin resistant diabetes, hyperlipidaemia and hyperphagia. Most importantly, the increased levels of 11βHSD1 activity in the fat of these mice are similar to those seen in obese subjects. Hepatic 11βHSD1 activity and plasma corticosterone levels were normal, however, hepatic portal vein levels of corticosterone were increased 3 fold and it is thought that this is the cause of the metabolic effects in liver.

Overall it is now clear that the complete metabolic syndrome can be mimicked in mice simply by overexpressing 11βHSD1 in fat alone at levels similar to those in obese man.

11βHSD1 tissue distribution is widespread and overlapping with that of the glucocorticoid receptor. Thus, 11βHSD1 inhibition could potentially oppose the effects of glucocorticoids in a number of physiological/pathological roles. 11βHSD1 is present in human skeletal muscle and glucocorticoid opposition to the anabolic effects of insulin on protein turnover and glucose metabolism are well documented (Whorwood C B et al. 2001; J. Clin. Endocrinol. Metab. 86, 2296-2308). Skeletal muscle must therefore be an important target for 11βHSD1 based therapy.

Glucocorticoids also decrease insulin secretion and this could exacerbate the effects of glucocorticoid induced insulin resistance. Pancreatic islets express 11βHSD1 and carbenoxolone can inhibit the effects of 11-dehydrocorticosterone on insulin release (Davani B et al. 2000; J. Biol. Chem. 275, 34841-34844). Thus in treatment of diabetes 11βHSD1 inhibitors may not only act at the tissue level on insulin resistance but also increase insulin secretion itself.

Skeletal development and bone function is also regulated by glucocorticoid action. 11βHSD1 is present in human bone osteoclasts and osteoblasts and treatment of healthy volunteers with carbenoxolone showed a decrease in bone resorption markers with no change in bone formation markers (Cooper M S et al 2000; Bone 27, 375-381). Inhibition of 11βHSD1 activity in bone could be used as a protective mechanism in treatment of osteoporosis.

Glucocorticoids may also be involved in diseases of the eye such as glaucoma. 11βHSD1 has been shown to affect intraocular pressure in man and inhibition of 11βHSD1 may be expected to alleviate the increased intraocular pressure associated with glaucoma (Rauz S et al. 2001; Investigative Ophthalmology & Visual Science 42, 2037-2042).

There appears to be a convincing link between 11βHSD1 and the metabolic syndrome both in rodents and in humans. Evidence suggests that a drug which specifically inhibits 11βHSD1 in type 2 obese diabetic patients will lower blood glucose by reducing hepatic gluconeogenesis, reduce central obesity, improve the atherogenic lipoprotein phenotype, lower blood pressure and reduce insulin resistance. Insulin effects in muscle will be enhanced and insulin secretion from the beta cells of the islet may also be increased.

Currently there are two main recognised definitions of metabolic syndrome.

1) The Adult Treatment Panel (ATP III 2001 JMA) definition of metabolic syndrome indicates that it is present if the patient has three or more of the following symptoms:
Waist measuring at least 40 inches (102 cm) for men, 35 inches (88 cm) for women;
Serum triglyceride levels of at least 150 mg/dl (1.69 mmol/l);
HDL cholesterol levels of less than 40 mg/dl (1.04 mmol/l) in men, less than 50 mg/dl (1.29 mmol/l) in women;
Blood pressure of at least 135/80 mm Hg; and/or Blood sugar (serum glucose) of at least 110 mg/dl (6.1 mmol/l).

2) The WHO consultation has recommended the following definition which does not imply causal relationships and is suggested as a working definition to be improved upon in due course:

The patient has at least one of the following conditions: glucose intolerance, impaired glucose tolerance (IGT) or diabetes mellitus and/or insulin resistance; together with two or more of the following:
Raised Arterial Pressure;
Raised plasma triglycerides
Central Obesity
Microalbuminuria

BRIEF SUMMARY OF THE INVENTION

We have found that the Agent, or a pharmaceutically-acceptable salt thereof, is an effective 11βHSD1 inhibitor, and accordingly has value in the treatment of disease states associated with metabolic syndrome. We have also found that the compound of the invention has improved properties, which would make it a better candidate for use as a pharmaceutical.

We have now discovered further crystalline forms of the Agent. These forms will be referred to as Form 2, Form 3 and Form 4.

DETAILED DESCRIPTION OF THE INVENTION

Accordingly one aspect of the invention relates to a crystalline form of 4-[4-(2-adamantylcarbamoyl)-5-tert-butyl-pyrazol-1-yl]benzoic acid (Form 2), which has an X-ray diffraction pattern measured with at least one specific peak at about 2-theta=18.0.

The 2-theta (θ) values were measured using CuKa radiation.

According to the present invention there is provided a crystalline form of the Agent, Form 2, which has an X-ray powder diffraction pattern with at least two specific peaks at about 2-theta=18.0° and 17.7°.

According to the present invention there is provided a crystalline form of the Agent, Form 2, which has an X-ray powder diffraction pattern with specific peaks at about 2-theta=18.0, 17.7 and 18.4°.

According to the present invention there is provided a crystalline form of the Agent, Form 2, which has an X-ray powder diffraction pattern with specific peaks at about 2-theta=18.0, 17.7, 18.4, 8.9 and 20.5°.

According to the present invention there is provided a crystalline form of the Agent, Form 2, which has an X-ray powder diffraction pattern with specific peaks at about 2-theta=18.0, 17.7, 18.4, 8.9, 20.5, 10.4, 21.9, 13.4, 27.6 and 16.7°.

Figure 1:
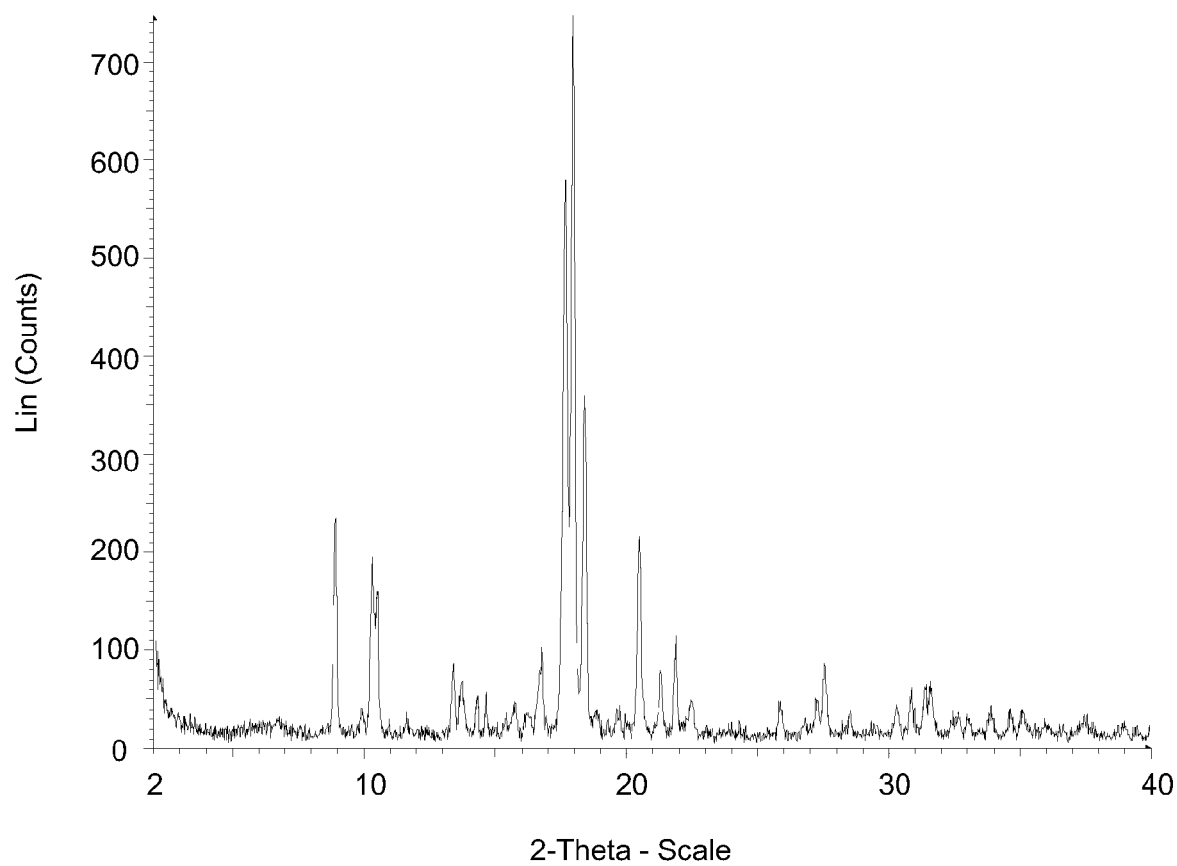
FIG. 1 shows an X-ray powder diffraction pattern of crystalline Form 2 of the Agent.

According to the present invention there is provided crystalline form of the Agent, Form 2 which has an X-ray powder diffraction pattern, using CuKa radiation, substantially the same as the X-ray powder diffraction pattern shown in FIG. 1.

According to the present invention there is provided a crystalline form of the Agent, Form 2, which has an X-ray powder diffraction pattern with at least one specific peak at 2-theta=18.0° plus or minus 0.5° 2-theta.

According to the present invention there is provided a crystalline form of the Agent, Form 2, which has an X-ray powder diffraction pattern with at least two specific peaks at 2-theta=18.0° and 17.7° wherein said values may be plus or minus 0.5° 2-theta.

According to the present invention there is provided a crystalline form of the Agent, Form 2, which has an X-ray powder diffraction pattern with specific peaks at 2-theta=18.0, 17.7 and 18.4° wherein said values may be plus or minus 0.5° 2-theta.

According to the present invention there is provided a crystalline form of the Agent, Form 2, which has an X-ray powder diffraction pattern with specific peaks at 2-theta=18.0, 17.7, 18.4, 8.9 and 20.5° wherein said values may be plus or minus 0.5° 2-theta.

According to the present invention there is provided a crystalline form of the Agent, Form 2, which has an X-ray powder diffraction pattern with specific peaks at 2-theta=18.0, 17.7, 18.4, 8.9, 20.5, 10.4, 21.9, 13.4, 27.6 and 16.7° wherein said values may be plus or minus 0.5° 2-theta.

According to the present invention there is provided a crystalline form of the Agent, Form 2, which has an X-ray powder diffraction pattern with at least one specific peak at 2-theta=18.0°.

According to the present invention there is provided a crystalline form of the Agent, Form 2, which has an X-ray powder diffraction pattern with at least two specific peaks at 2-theta=18.0 and 17.7°.

According to the present invention there is provided crystalline form of the Agent, Form 2, which has an X-ray powder diffraction pattern with specific peaks at 2-theta=18.0, 17.7 and 18.4°.

According to the present invention there is provided crystalline form of the Agent, Form 2, which has an X-ray powder diffraction pattern with specific peaks at 2-theta=18.0, 17.7, 18.4, 8.9 and 20.5°

According to the present invention there is provided crystalline form of the Agent, Form 2, which has an X-ray powder diffraction pattern with specific peaks at 2-theta=18.0, 17.7, 18.4, 8.9, 20.5, 10.4, 21.9, 13.4, 27.6 and 16.7°.

According to the present invention there is provided crystalline form of the Agent, Form 2, which has an X-ray powder diffraction pattern, using CuKa radiation, as shown in FIG. 1.

TABLE A

Ten most Prominent X-Ray Powder Diffraction peaks Form 2 of the Agent

| Angle 2-Theta (2θ) | Intensity % | Relative Intensity |
| --- | --- | --- |
| 17.954 | 100 | vs |
| 17.656 | 77.4 | vs |
| 18.414 | 47.9 | vs |
| 8.869 | 30.5 | vs |
| 20.498 | 28.7 | vs |
| 10.415 | 21.3 | s |
| 21.880 | 15.1 | s |
| 13.391 | 11.4 | s |

TABLE A-continued

Ten most Prominent X-Ray Powder Diffraction peaks Form 2 of the Agent

| Angle 2-Theta (2θ) | Intensity % | Relative Intensity |
| --- | --- | --- |
| 27.576 | 11.4 | s |
| 16.729 | 10.8 | s | vs = very strong
s = strong

Figure 2:
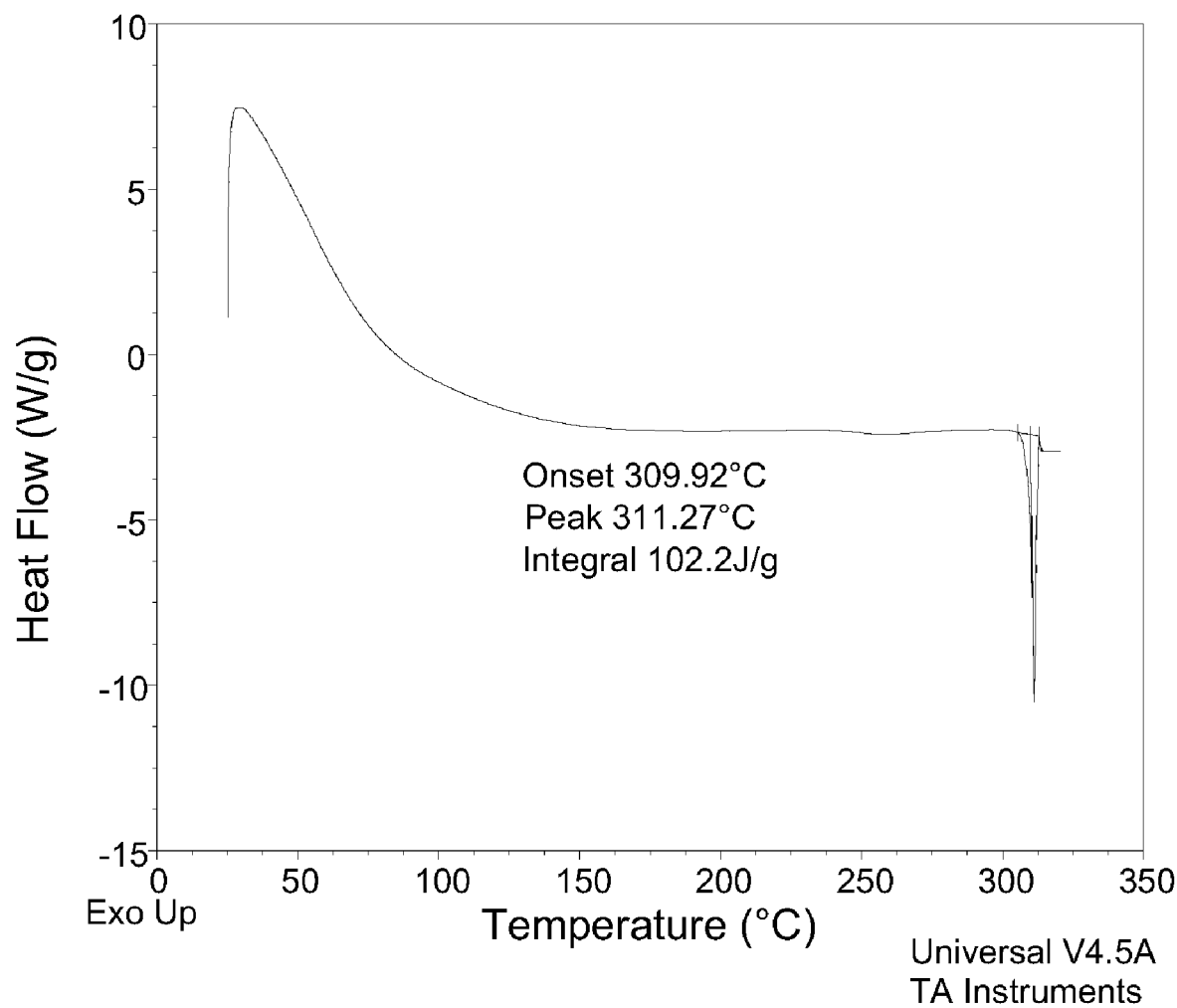
FIG. 2 depicts a DSC thermogram of crystalline Form 2 of the Agent.

DSC analysis shows Form 2 is a high melting solid with an onset of melting at 309.9 C. The DSC thermogram is depicted in FIG. 2

According to the present invention there is provided a crystalline form of the Agent, Form 3, which has an X-ray powder diffraction pattern with at a peak at about 2-theta=18.7°.

The 2-theta (θ) values were measured using CuKa radiation.

According to the present invention there is provided a crystalline form of the Agent, Form 3, which has an X-ray powder diffraction pattern with at least two specific peaks at about 2-theta=18.7° and 11.7°.

According to the present invention there is provided a crystalline form of the Agent, Form 3, which has an X-ray powder diffraction pattern with specific peaks at about 2-theta=18.7, 11.7 and 19.2°.

According to the present invention there is provided a crystalline form of the Agent, Form 3, which has an X-ray powder diffraction pattern with specific peaks at about 2-theta=18.7, 11.7, 19.2, 7.8, 14.1, 14.9 and 9.4°.

According to the present invention there is provided a crystalline form of the Agent, Form 3, which has an X-ray powder diffraction pattern with specific peaks at about 2-theta=18.7, 11.7, 19.2, 7.8, 14.1, 14.9, 9.4, 15.6, 16.1 and 9.6°.

Figure 3:
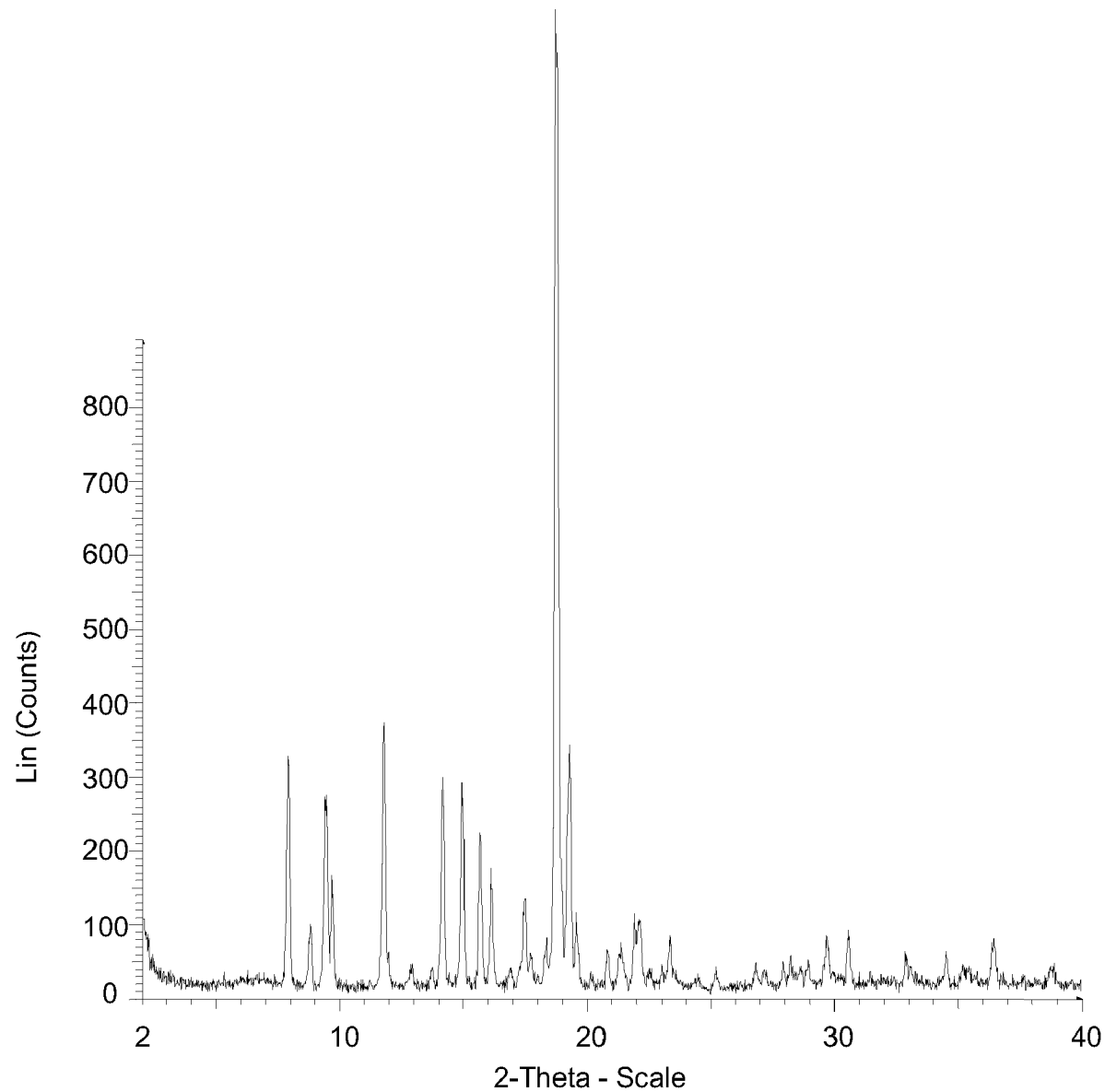
FIG. 3 shows an X-ray powder diffraction pattern of crystalline Form 3 of the Agent.

According to the present invention there is provided crystalline form of the Agent, Form 3, which has an X-ray powder diffraction pattern, using CuKa radiation, substantially the same as the X-ray powder diffraction pattern shown in FIG. 3.

According to the present invention there is provided a crystalline form of the Agent, Form 3, which has an X-ray powder diffraction pattern with at least one specific peak at 2-theta=18.7° plus or minus 0.5° 2-theta.

According to the present invention there is provided a crystalline form of the Agent, Form 3, which has an X-ray powder diffraction pattern with at least two specific peaks at 2-theta=18.7° and 11.7° wherein said values may be plus or minus 0.5° 2-theta.

According to the present invention there is provided a crystalline form of the Agent, Form 3, which has an X-ray powder diffraction pattern with specific peaks at 2-theta=18.7, 11.7 and 19.2° wherein said values may be plus or minus 0.5° 2-theta.

According to the present invention there is provided a crystalline form of the Agent, Form 3, which has an X-ray powder diffraction pattern with specific peaks at 2-theta=18.7, 11.7, 19.2, 7.8, 14.1, 14.9 and 9.4° wherein said values may be plus or minus 0.5° 2-theta.

According to the present invention there is provided a crystalline form of the Agent, Form 3, which has an X-ray powder diffraction pattern with specific peaks at 2-theta=18.7, 11.7, 19.2, 7.8, 14.1, 14.9, 15.6, 16.1 and 9.6° wherein said values may be plus or minus 0.5° 2-theta.

According to the present invention there is provided a crystalline form of the Agent, Form 3, which has an X-ray powder diffraction pattern with at least one specific peak at 2-theta=18.7°.

According to the present invention there is provided a crystalline form of the Agent, Form 3, which has an X-ray powder diffraction pattern with at least two specific peaks at 2-theta=18.7 and 11.7°.

According to the present invention there is provided crystalline form of the Agent, Form 3, which has an X-ray powder diffraction pattern with specific peaks at 2-theta=18.7, 11.7 and 19.2°.

According to the present invention there is provided crystalline form of the Agent, Form 3, which has an X-ray powder diffraction pattern with specific peaks at 2-theta=18.7, 11.7, 19.2, 7.8, 14.1, 14.9, 9.4°.

According to the present invention there is provided crystalline form of the Agent, Form 3, which has an X-ray powder diffraction pattern with specific peaks at 2-theta=18.7, 11.7, 19.2, 7.8, 14.1, 14.9, 9.4, 15.6, 16.1 and 9.6°.

According to the present invention there is provided crystalline form of the Agent, Form 3, which has an X-ray powder diffraction pattern, using CuKa radiation, as shown in FIG. 3.

TABLE B

Ten most Prominent X-Ray Powder Diffraction peaks Form 3 of the Agent

| Angle 2-Theta (2θ) | Intensity % | Relative Intensity |
|---|---|---|
| 18.694 | 100.0 | vs |
| 11.704 | 32.0 | vs |
| 19.209 | 29.9 | vs |
| 7.810 | 28.8 | vs |
| 14.084 | 26.8 | vs |
| 14.892 | 26.3 | vs |
| 9.351 | 25.1 | vs |
| 15.598 | 21.5 | s |
| 16.079 | 18.1 | s |
| 9.610 | 17.5 | s | vs = very strong
s = strong

Figure 4:
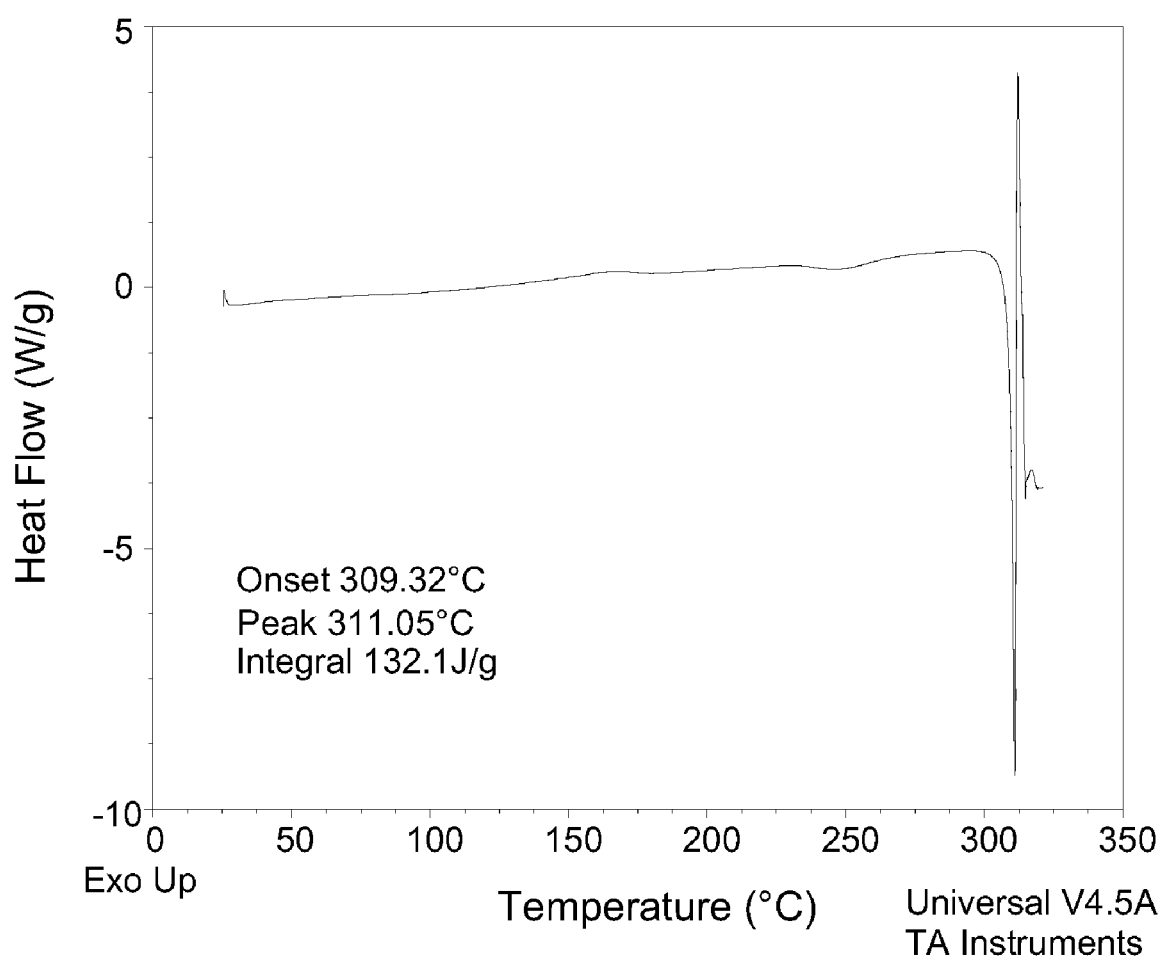
FIG. 4 depicts a DSC thermogram of crystalline Form 3 of the Agent.

DSC analysis shows Form 3 has an onset of melting at 309.3° C. The DSC thermogram is depicted in FIG. 4.

According to the present invention there is provided a crystalline form of the Agent, Form 4, which has an X-ray powder diffraction pattern with at a peak at about 2-theta=16.2°.

The 2-theta (θ) values were measured using CuKa radiation.

According to the present invention there is provided a crystalline form of the Agent, Form 4, which has an X-ray powder diffraction pattern with at least two specific peaks at about 2-theta=16.2° and 20.6°.

According to the present invention there is provided a crystalline form of the Agent, Form 4, which has an X-ray powder diffraction pattern with specific peaks at about 2-theta=16.2, 20.6 and 17.7°.

According to the present invention there is provided a crystalline form of the Agent, Form 4, which has an X-ray powder diffraction pattern with specific peaks at about 2-theta=16.2, 20.6, 17.7, 10.8 and 15.5°.

According to the present invention there is provided a crystalline form of the Agent, Form 4, which has an X-ray powder diffraction pattern with specific peaks at about 2-theta=16.2, 20.6, 17.7, 10.8, 15.5, 20.9, 26.1, 11.6, 26.7 and 18.1°.

Figure 5:
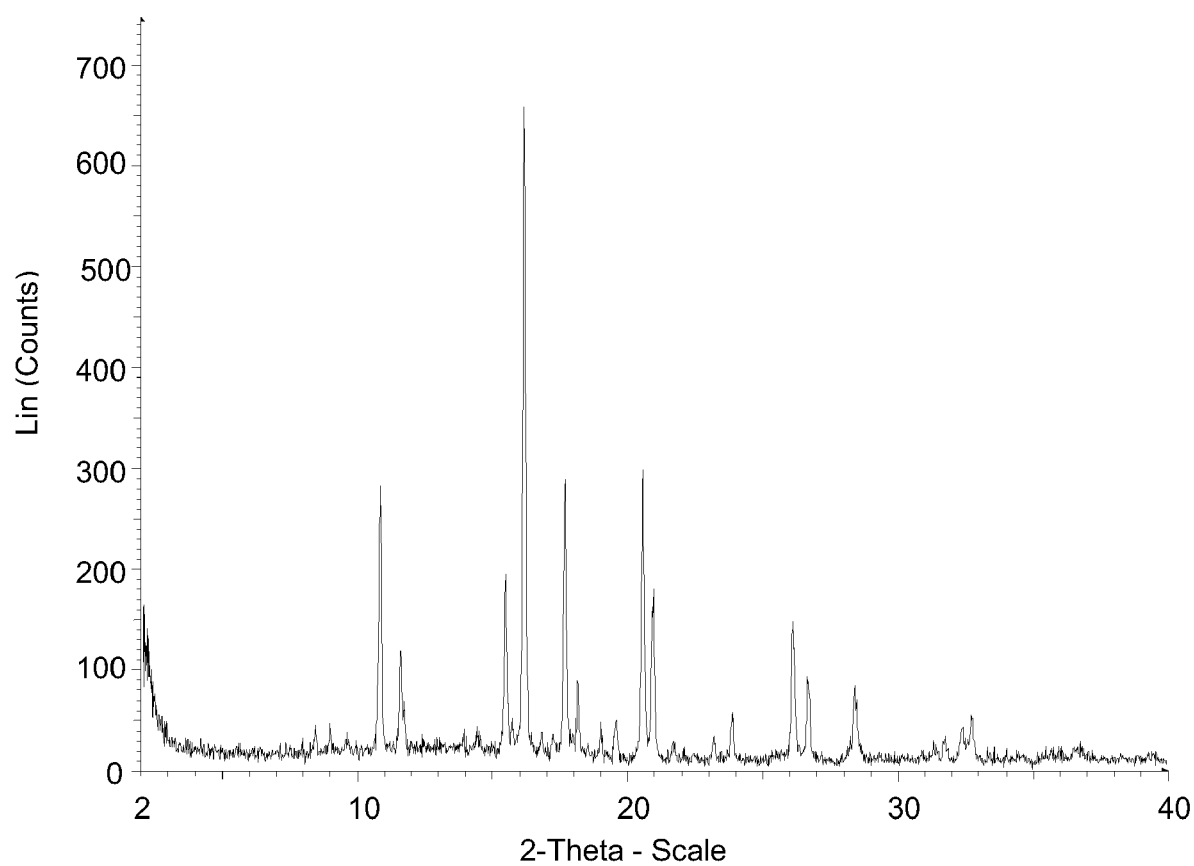
FIG. 5 shows an X-ray powder diffraction pattern of crystalline Form 4 of the Agent.

According to the present invention there is provided crystalline form of the Agent, Form 4 which has an X-ray powder diffraction pattern, using CuKa radiation, substantially the same as the X-ray powder diffraction pattern shown in FIG. 5.

According to the present invention there is provided a crystalline form of the Agent, Form 4, which has an X-ray powder diffraction pattern with at least one specific peak at 2-theta=16.2° plus or minus 0.5° 2-theta.

According to the present invention there is provided a crystalline form of the Agent, Form 4, which has an X-ray powder diffraction pattern with at least two specific peaks at 2-theta=16.2° and 20.6° wherein said values may be plus or minus 0.5° 2-theta.

According to the present invention there is provided a crystalline form of the Agent, Form 4, which has an X-ray powder diffraction pattern with specific peaks at 2-theta=16.2, 20.6 and 17.7° wherein said values may be plus or minus 0.5° 2-theta.

According to the present invention there is provided a crystalline form of the Agent, Form 4, which has an X-ray powder diffraction pattern with specific peaks at 2-theta=16.2, 20.6, 17.7, 10.8 and 15.5° wherein said values may be plus or minus 0.5° 2-theta.

According to the present invention there is provided a crystalline form of the Agent, Form 4, which has an X-ray powder diffraction pattern with specific peaks at 2-theta=16.2, 20.6, 17.7, 10.8, 15.5, 20.9, 26.1, 11.6, 26.7 and 18.1° wherein said values may be plus or minus 0.5° 2-theta.

According to the present invention there is provided a crystalline form of the Agent, Form 4, which has an X-ray powder diffraction pattern with at least one specific peak at 2-theta=16.2°.

According to the present invention there is provided a crystalline form of the Agent, Form 4, which has an X-ray powder diffraction pattern with at least two specific peaks at 2-theta=16.2 and 20.6°.

According to the present invention there is provided crystalline form of the Agent, Form 4, which has an X-ray powder diffraction pattern with specific peaks at 2-theta=16.2, 20.6 and 17.7°.

According to the present invention there is provided crystalline form of the Agent, Form 4, which has an X-ray powder diffraction pattern with specific peaks at 2-theta=16.2, 20.6, 17.7, 10.8 and 15.5°.

According to the present invention there is provided crystalline form of the Agent, Form 4, which has an X-ray powder diffraction pattern with specific peaks at 2-theta=16.2, 20.6, 17.7, 10.8, 15.5, 20.9, 26.1, 11.6 and 26.7°.

According to the present invention there is provided crystalline form of the Agent, Form 4, which has an X-ray powder diffraction pattern, using CuKa radiation, as shown in FIG. 5.

TABLE C

Ten most Prominent X-Ray Powder Diffraction peaks Form 4 of the Agent

| Angle 2-Theta (2θ) | Intensity % | Relative Intensity |
|---|---|---|
| 16.165 | 100.0 | vs |
| 20.567 | 45.2 | vs |
| 17.652 | 43.7 | vs |
| 10.826 | 42.8 | vs |
| 15.476 | 29.4 | vs |
| 20.944 | 24.6 | s |
| 26.131 | 22.3 | s |
| 11.588 | 17.9 | s |

TABLE C-continued

Ten most Prominent X-Ray Powder Diffraction
peaks Form 4 of the Agent

| Angle 2-Theta (2θ) | Intensity % | Relative Intensity |
|---|---|---|
| 26.709 | 13.5 | s |
| 18.138 | 13.4 | s | vs = very strong
s = strong

Figure 6:
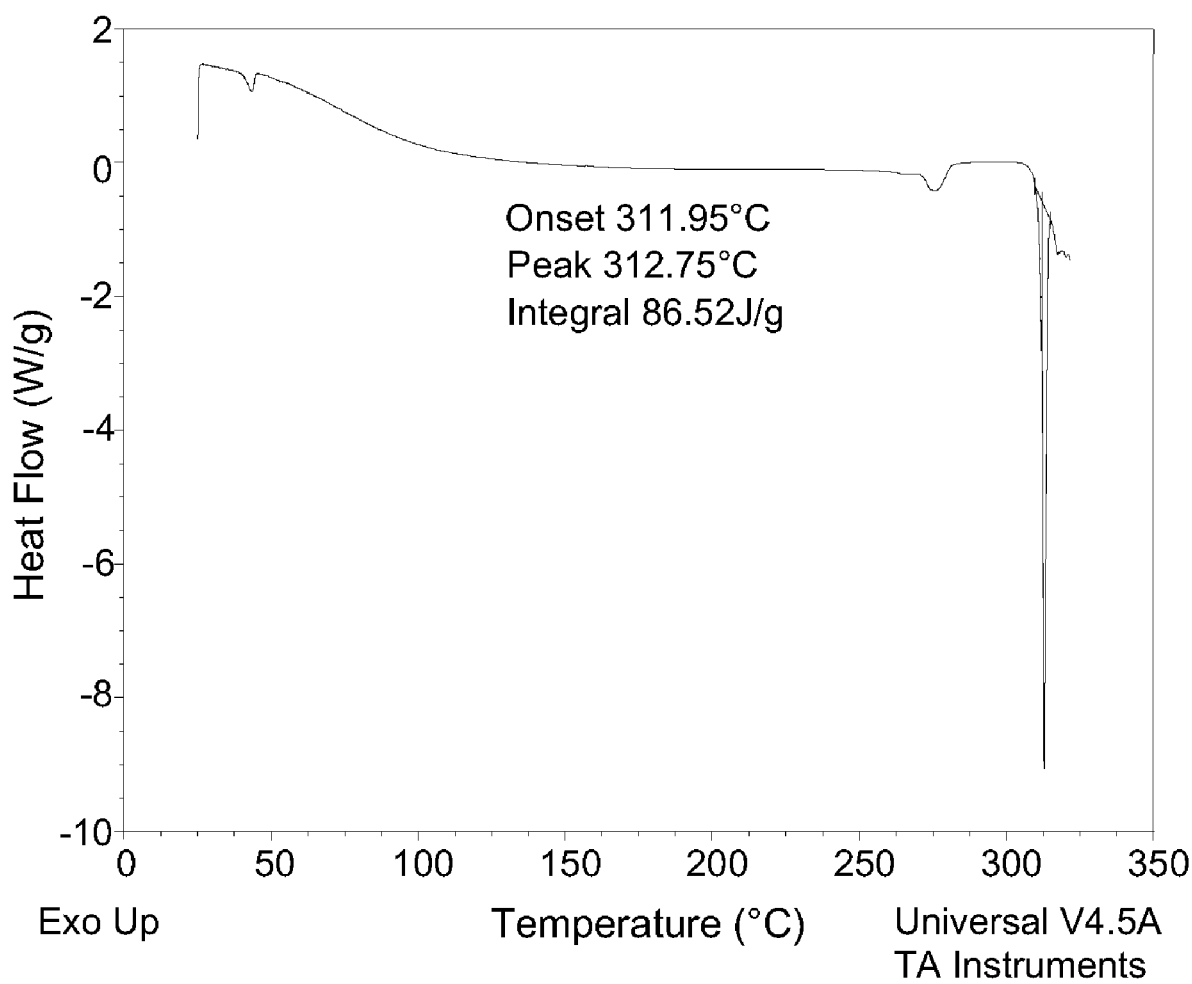
FIG. 6 depicts a DSC thermogram of crystalline Form 4 of the Agent.

DSC analysis of Form 4 shows an initial event with an onset at 254.0° C. and a peak at 262.0° C. followed by a subsequent melt with an onset of 312.0° C. Thus onset of melting of Form 4 is at about 312.0° C. The DSC thermogram is depicted in FIG. 6.

Figure 7:
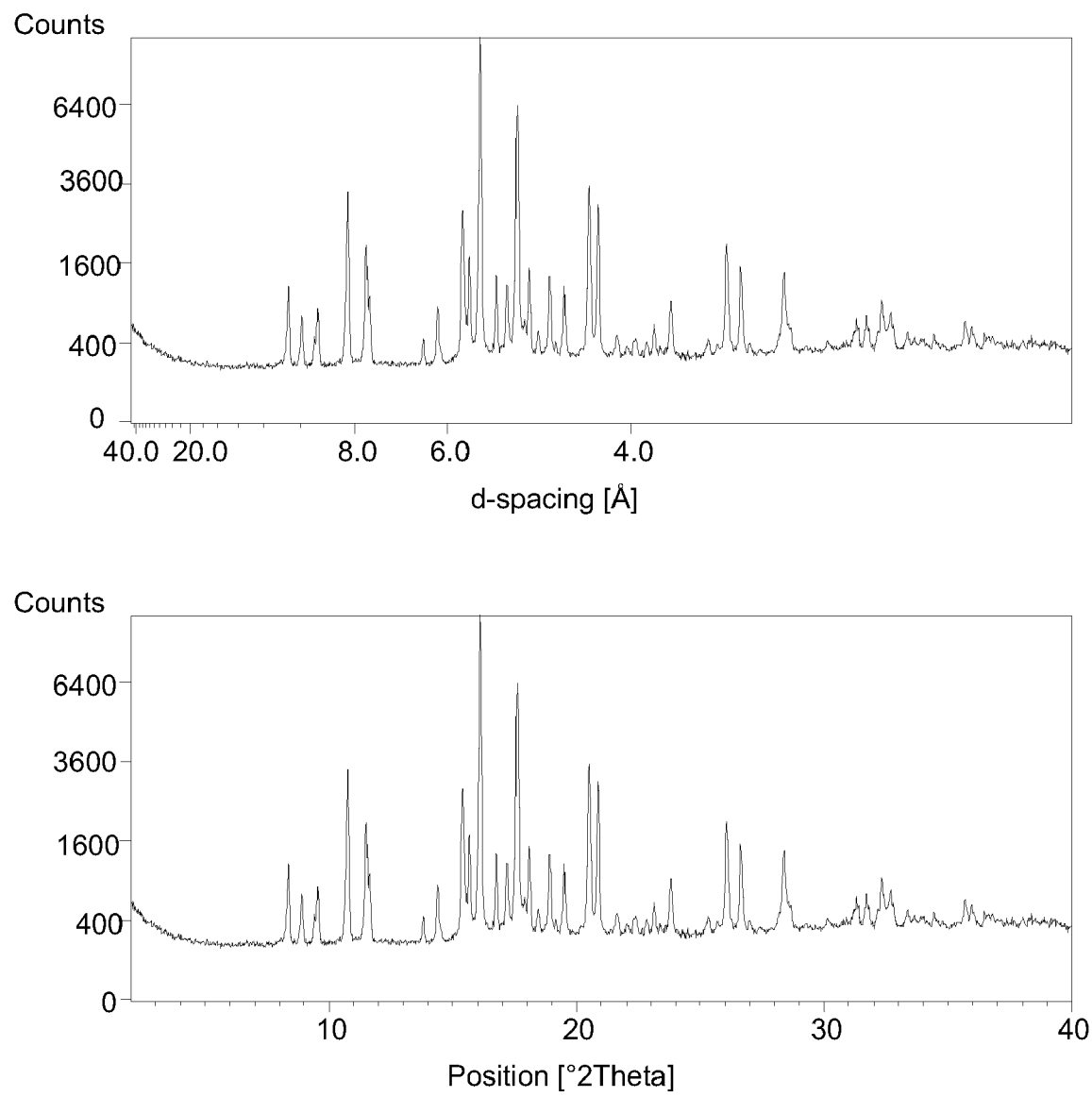
FIG. 7 depicts a DSC thermogram of a more pure sample of crystalline Form 4 of the Agent.

Another more pure sample of form 4 gave the XRD pattern and d-spacing spectrum shown in FIG. 7. The position of the 2-theta values and the d-spacing are shown in tables D and E respectively.

TABLE D

| Diffraction Peaks for form 4 Pos. [°2Th.] |
|---|
| 10.8 |
| 11.5 |
| 15.4 |
| 16.1 |
| 17.6 |
| 18.9 |
| 20.5 |
| 20.9 |
| 26.1 |
| 26.6 |

TABLE E

| d-Spacing for form 4 d-spacing [Å] |
|---|
| 8.2 |
| 7.7 |
| 5.8 |
| 5.5 |
| 5.0 |
| 4.7 |
| 4.3 |
| 4.3 |
| 3.4 |
| 3.3 |

The slight variation in 2-theta values in tables C and D may be due to a measurement error of a diffraction angle in an X-ray powder diffractogram as mentioned hereinbelow.

Thus in another aspect of the invention allowing for measurement error, there is provided a crystalline form of the Agent, Form 4, which has an X-ray powder diffraction pattern with at least two specific peaks at 2-theta=16.1 and 20.5°.

According to the present invention there is provided crystalline form of the Agent, Form 4, which has an X-ray powder diffraction pattern with specific peaks at 2-theta=16.1, 20.5 and 17.6°.

According to the present invention there is provided crystalline form of the Agent, Form 4, which has an X-ray powder diffraction pattern with specific peaks at 2-theta=16.1, 20.5, 17.6, 10.8 and 15.4°.

According to the present invention there is provided crystalline form of the Agent, Form 4, which has an X-ray powder diffraction pattern with specific peaks at 2-theta=16.1, 20.5, 17.6, 10.8, 15.4, 20.9 and 26.1°.

When it is stated that the present invention relates to a crystalline form of Forms 2, 3 and 4, the degree of crystallinity is conveniently greater than about 60%, more conveniently greater than about 80%, preferably greater than about 90% and more preferably greater than about 95%. Most preferably the degree of crystallinity is greater than about 98%.

In another aspect the invention relates to the Agent as a crystalline form 2.

In another aspect the invention relates to the Agent as a crystalline form 3.

In another aspect the invention relates to the Agent as a crystalline form 4.

In another aspect the invention relates to a crystalline form 2 of the Agent substantially free of crystalline form 1.

In another aspect the invention relates to a crystalline form 3 of the Agent substantially free of crystalline form 1.

In another aspect the invention relates to a crystalline form 4 of the Agent substantially free of crystalline form 1.

A crystalline form substantially free of form 1 means a crystalline form having less than 30% form 1. In another aspect, 'substantially free', means having less that 20% form 1. In another aspect, 'substantially free', means having less that 10% form 1. In yet another aspect, 'substantially free', means having less that 5% form 1. In yet another aspect, 'substantially free', means having less that 1% form 1.

The Forms 2, 3 and 4 provide X-ray powder diffraction patterns substantially the same as the X-ray powder diffraction patterns shown in FIGS. 1, 2 and 3 and has substantially the ten most prominent peaks (angle 2-theta values) shown in Tables A, B and C. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the Forms 2, 3 and 4 of the present invention are not limited to the crystals that provide X-ray powder diffraction patterns identical to the X-ray powder diffraction pattern shown in FIGS. 1, 2 and 3, and any crystals providing X-ray powder diffraction patterns substantially the same as those shown in FIGS. 1, 2 and 3 fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is about 5% or less, in particular plus or minus 0.5° 2-theta. Typically plus or minus 0.2°

2-theta. Such degree of a measurement error should be taken into account when considering the X-ray powder diffraction patterns in FIGS. 1, 2, 3 and 4 and when reading Tables A, B, C and D. Furthermore, it should be understood that intensities might fluctuate depending on experimental conditions and sample preparation (preferred orientation).

Details of Techniques Used
X-Ray Powder Diffraction

TABLE B

| % Relative Intensity* | Definition |
| --- | --- |
| 25-100 | vs (very strong) |
| 10-25 | s (strong) |
| 3-10 | m (medium) |
| 1-3 | w (weak) |

*The relative intensities are derived from diffractograms measured with fixed slits Analytical Instrument: Siemens D5000.

The X-ray powder diffraction spectra were determined by mounting a sample of the crystalline material on a Siemens single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The running time was 31 minutes and 41 seconds. The instrument was equipped with a scintillation counter as detector. Control and data capture was by means of a Dell Optiplex 686 NT 4.0 Workstation operating with Diffract+ software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry

Analytical Instrument: TA Instruments Q1000 DSC.

Typically less than 5 mg of material contained in a 40 μl aluminium pan fitted with a lid was heated over the temperature range 25° C. to 325° C. at a constant heating rate of 10° C. per minute. A purge gas using nitrogen was used—flow rate 100 ml per minute.

Forms 2, 3 and 4 may be prepared by competitive slurring from form 1 or seeding. Conveniently form 2 may be prepared by competitive slurrying in acetonitrile. In particular, this is carried out in a temperature range of 45-55° C., for example about 50° C. Conveniently form 3 may be prepared by competitive slurrying in methanol. In particular, this is carried out in a temperature range of 15-30° C., for example about ambient. Conveniently form 4 may be prepared by competitive slurrying in ethyl acetate. In particular, this is carried out in a temperature range of 15-30° C., for example about ambient. In addition, form 4 may be prepared by competitive slurrying in acetone or acetonitrile at elevated temperatures.

As stated hereinbefore the Agent possesses 11βHSD1 inhibitory activity. These properties may be assessed using the following assay.

Assays

The conversion of cortisone to the active steroid cortisol by 11βHSD1 oxo-reductase activity, can be measured using a competitive homogeneous time resolved fluorescence assay (HTRF) (CisBio International, R&D, Administration and Europe Office, In Vitro Technologies—HTRF®/Bioassays BP 84175, 30204 Bagnols/Ceze Cedex, France. Cortisol bulk HTRF kit: Cat No. 62CORPEC).

The evaluation of the compound described herein was carried out using a baculovirus expressed N terminal 6-His tagged full length human 11βHSD1 enzyme (*1). The enzyme was purified from a detergent solublised cell lysate, using a copper chelate column. Inhibitors of 11βHSD1 reduce the conversion of cortisone to cortisol, which is identified by an increase in signal, in the above assay.

*1 The Journal of Biological Chemistry, Vol. 26, No 25, pp 16653-16658

The compound to be tested was dissolved in dimethyl sulphoxide (DMSO) to 10 mM and diluted further in assay buffer containing 1% DMSO to 10 fold the final assay concentration. Diluted compound was then plated into black 384 well plates (Matrix, Hudson N.H., USA).

The assay was carried out in a total volume of 20 μl consisting of cortisone (Sigma, Poole, Dorset, UK, 160 nM), glucose-6-phosphate (Roche Diagnostics, 1 mM), NADPH (Sigma, Poole, Dorset, 100 μM), glucose-6-phosphate dehydrogenase (Roche Diagnostics, 12.5 μg/ml), EDTA (Sigma, Poole, Dorset, UK, 1 mM), assay buffer ($K_2HPO_4/KH_2PO_4$, 100 mM) pH 7.5, recombinant 11βHSD1 [using an appropriate dilution to give a viable assay window—an example of a suitable dilution may be 1 in 1000 dilution of stock enzyme] plus test compound. The assay plates were incubated for 25 minutes at 37° C. after which time the reaction was stopped by the addition of 10 μl of 0.5 mM glycerrhetinic acid plus conjugated cortisol (XL665 or D2). 10 μl of anti-cortisol Cryptate was then added and the plates sealed and incubated for 6 hours at room temperature. Fluorescence at 665 nm and 620 nm was measured and the 665 nm:620 nm ratio calculated using an Envision plate reader.

These data were then used to calculate $IC_{50}$ values for each compound (Origin 7.5, Microcal software, Northampton Mass., USA) and/or the % inhibition at 30 μM of compound.

The following results were obtained: Reference Example 1 IC50 0.008 μM.

The oral bioavailability of the compound of the invention may be tested as follows:

Determination of Bioavailability in PK Studies

Compounds are dosed intravenously at 2 mg/kg (2 ml/kg) and orally at 5 mg/kg (5 ml/kg) in a 25% HPBCD in sorrensons buffer pH 5.5 formulation. Blood samples (200 ul) are taken Predose, 0.25, 0.5, 1, 2, 3, 4, 5, 6, 8 and 24 h post dose for both routes and plasma prepared by centrifugation. Plasma samples are analysed as below. PK parameters (clearance, volume of distribution, bioavailability, fraction absorbed etc.) are calculated by standard PK methods using suitable PK software (WinNon-Lin).

Bioanalysis of Plasma Samples

The guidelines described are for the manual preparation of plasma samples following single compound or cassette dosing of project compounds to all PK species used within discovery DMPK. Analysis by open access (LC-MS/MS) or manual approaches (LC-MS) is described.

Contents
1. Materials
2. Generic Extraction Method
3. Example Sample List Using Generic Plate Layout
4. Open Access Batch Submission and System Checks
5. Acceptance Criteria for Batch Pass 1. Materials
Solvents: Methanol, acetonitrile and DMSO
Water: Purified or HPLC grade
1 ml shallow 96-well plates OR eppendorf tubes
2 ml deep well 96-well plates plus lids
Blank (control) plasma 2. Generic Extraction Method
Solubilise compound(s) to 1 mg/ml using DMSO taking into account salt factors if any.
The DMSO stock(s) may be used to make all calibration & quality control (QC) samples:

2.i Single Compound Analysis
2.i.a Preparation of Calibration and QC Samples:
1. Prepare standard solutions as follows:

| Stock diluted ng/ml | Volume methanol ml | Volume stock ml | Standard conc. ng/ml | Post plasma dilution conc. ng/ml |
|---|---|---|---|---|
| 1 mg/ml | 0.9 | 0.1 | 100,000 | 10,000 |
| 100,000 | 0.5 | 0.5 | 50,000 | 5,000 |
| 50,000 | 0.75 | 0.5 | 20,000 | 2,000 |
| 20,000 | 0.5 | 0.5 | 10,000 | 1,000 |
| 10,000 | 0.5 | 0.5 | 5,000 | 500 |
| 5,000 | 2 | 0.5 | 1,000 | 100 |
| 1,000 | 0.5 | 0.5 | 500 | 50 |
| 500 | 0.75 | 0.5 | 200 | 20 |
| 200 | 0.5 | 0.5 | 100 | 10 |
| 100 | 0.5 | 0.5 | 50 | 5 |
| 50 | 0.5 | 0.5 | 10 | 1 |

2. Transfer 50 ul blank plasma to a well of a 1 ml 96-well plate (shallow well)
3. Transfer 5 ul of each of the standard solutions to further wells of the plate
4. Add 50 ul blank plasma to each of these wells.
5. To generate the QC samples, add three aliquots of 5 ul of the 100 ng/ml, 1000 ng/ml and 10,000 ng/ml standard solutions to the plate (3 QCs at each concentration).
6. Add 50 ul blank plasma to each of these.
7. Transfer 50 ul of each PK sample to the 1 ml 96-well plate
8. Add 5 ul methanol (-compound) to each of the PK samples
9. Ensure all dose formulations are well mixed by vortex mixing.
10. Dilute intravenous (IV) and oral dose (PO) formulations of expected concentration to 10 ug/ml in methanol. (For example, a formulation made to an expected concentration of 2 mg/ml would be diluted 1:200 to give 10 ug/ml solution).
11. Add 6×50 ul aliquots of plasma to the plate. Add 5 ul of diluted IV formulation to three of the wells, repeat with PO formulation and remaining 3 wells.
12. Precipitate proteins by adding 100 ul acetonitrile containing a project related internal standard (at 1 ug/ml) to all calibration, QC, PK and formulation samples.
13. Vortex mix the plate before centrifugation at 4,000 g for 10 minutes.
14. Transfer 100 ul of the supernatant to the wells of a 2 ml 96-well plate (see following plate map). Care should be taken not to disturb the pellet.
15. Add ~1.5 ml of 50:50 Methanol:Water into the last well.
16. For analysis on triple quad systems: add 400 ul water (HPLC grade) to each sample. Gently mix.
17. Add 100 ul of the 100,000 ng/ml stock of each of the standard solutions to the 2 ml plate and add 900 ul water. Add a sample of internal standard to a further well (see plate map). These are for compound tuning (denoted on the plate map as tune solutions)
18. For analysis on platform systems: add 100 ul water (HPLC grade) to each sample. Gently mix.
19. Manually tune all compounds using compound solutions prepared to 5,000 ng/ml (add 100 ul of the 50,000 ng/ml standard solutions to 900 ul water)

2.ii Cassette Dose Analysis
2.iia Preparation of Calibration and QC Samples:
Note: For cassette dosing, the amount of methanol required to dilute the 1 mg/ml stock will be adjusted according to the number of compounds present.
1. Add 100 ul of each 1 mg/ml stock required to a vial.
2. Add the required volume of methanol to yield a total volume of 1 ml.
3. Perform all further steps as for single compound analysis (steps 2-16 above).

2.iii In Cases where Pk Samples Exceed the Upper Limit of Quantification (ULOQ).
1. Prepare a further calibration curve and QC samples as above (steps 1-6).
2. Transfer <50 ul (e.g. 25 ul) of the PK samples that exceed the ULOQ.
3. Add enough control plasma to these samples to yield a final plasma volume of 50 ul. Make a note of the dilution made.
4. Transfer 50 ul of all remaining PK samples.
5. Prepare all formulation samples and extract all samples as described above. (steps 8-16)
Note: Upper concentrations used to generate the calibration curve may be reviewed, however, care must be taken to avoid saturation of the HPLC column or MS equipment. It is for this reason that dilution of PK samples is recommended.

2.1v In Cases of Poor Sensitivity (High Lower Limit of Quantification).
Note: High LLOQ is taken as when most of the plasma concentrations lie below the lower limit of quantification or where the LLOQ is greater the 10 ng/ml. The following methods should be applied when either of these scenarios is encountered.

According to a further aspect of the invention there is provided a pharmaceutical composition, which comprises the Agent, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In general, compositions in a form suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient. For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

We have found that the Agent, or a pharmaceutically-acceptable salt thereof, is an effective 11βHSD1 inhibitor, and accordingly has value in the treatment of disease states associated with metabolic syndrome.

It is to be understood that where the term "metabolic syndrome" is used herein, this relates to metabolic syndrome as defined in 1) and/or 2) or any other recognised definition of this syndrome. Synonyms for "metabolic syndrome" used in the art include Reaven's Syndrome, Insulin Resistance Syndrome and Syndrome X. It is to be understood that where the term "metabolic syndrome" is used herein it also refers to Reaven's Syndrome, Insulin Resistance Syndrome and Syndrome X.

According to a further aspect of the present invention there is provided the Agent, or a pharmaceutically-acceptable salt thereof, as defined hereinbefore for use in a method of prophylactic or therapeutic treatment of a warm-blooded animal, such as man.

Thus according to this aspect of the invention there is the Agent, or a pharmaceutically-acceptable salt thereof, for use as a medicament.

According to another feature of the invention there is provided the use of the Agent, or a pharmaceutically-acceptable salt thereof, in the manufacture of a medicament for use in the production of an 11βHSD1 inhibitory effect in a warm-blooded animal, such as man.

Where production of or producing an 11βHSD1 inhibitory effect is referred to suitably this refers to the treatment of metabolic syndrome. Alternatively, where production of an 11βHSD1 inhibitory effect is referred to this refers to the treatment of diabetes, obesity, hyperlipidaemia, hyperglycaemia, hyperinsulinemia or hypertension, particularly type 2 diabetes and obesity. Alternatively, where production of an 11βHSD1 inhibitory effect is referred to this refers to the treatment of glaucoma, osteoporosis, tuberculosis, dementia, cognitive disorders or depression.

Alternatively, where production of an 11βHSD1 inhibitory effect is referred to this refers to the treatment of cognitive disorders, such as improving the cognitive ability of an individual, for example by improvement of verbal fluency, verbal memory or logical memory, or for treatment of mild cognitive disorders. See for example WO03/086410 and references contained therein, and Proceedings of National Academy of Sciences (PNAS), 2001, 98(8), 4717-4721.

Alternatively, where production of an 11βHSD1 inhibitory effect is referred to this refers to the treatment of, delaying the onset of and/or reducing the risk of atherosclerosis—see for example J. Experimental Medicine, 2005, 202(4), 517-527.

Alternatively, where production of an 11βHSD1 inhibitory effect is referred to this refers to the treatment of Alzheimers and/or neurodegenerative disorders.

According to a further feature of this aspect of the invention there is provided a method for producing an 11βHSD1 inhibitory effect in a warm-blooded animal, such as man, in need of such treatment which comprises administering to said animal an effective amount of a compound of formula (I), or a pharmaceutically-acceptable salt thereof.

In addition to their use in therapeutic medicine, the Agent, or a pharmaceutically-salt thereof, are also useful as pharmacological tools in the development and standardisation of in vitro and in vivo test systems for the evaluation of the effects of inhibitors of 11βHSD1 in laboratory animals such as cats, dogs, rabbits, monkeys, rats and mice, as part of the search for new therapeutic agents.

The inhibition of 11βHSD1 described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example agents than might be co-administered with 11βHSD1 inhibitors, particularly those of the present invention, may include the following main categories of treatment:

1) Insulin and insulin analogues;
2) Insulin secretagogues including sulphonylureas (for example glibenclamide, glipizide), prandial glucose regulators (for example repaglinide, nateglinide), glucagon-like peptide 1 agonist (GLP1 agonist) (for example exenatide, liraglutide) and dipeptidyl peptidase IV inhibitors (DPP-IV inhibitors);
3) Insulin sensitising agents including PPARγ agonists (for example pioglitazone and rosiglitazone);
4) Agents that suppress hepatic glucose output (for example metformin);
5) Agents designed to reduce the absorption of glucose from the intestine (for example acarbose);
6) Agents designed to treat the complications of prolonged hyperglycaemia; e.g. aldose reductase inhibitors
7) Other anti-diabetic agents including phosotyrosine phosphatase inhibitors, glucose 6-phosphatase inhibitors, glucagon receptor antagonists, glucokinase activators, glycogen phosphorylase inhibitors, fructose 1,6 bisphosphastase inhibitors, glutamine:fructose-6-phosphate amidotransferase inhibitors
8) Anti-obesity agents (for example sibutramine and orlistat);
9) Anti-dyslipidaemia agents such as, HMG-CoA reductase inhibitors (statins, eg pravastatin); PPARα agonists (fibrates, eg gemfibrozil); bile acid sequestrants (cholestyramine); cholesterol absorption inhibitors (plant stanols, synthetic inhibitors); ileal bile acid absorption inhibitors (IBATi), cholesterol ester transfer protein inhibitors and nicotinic acid and analogues (niacin and slow release formulations);
10) Antihypertensive agents such as, β blockers (eg atenolol, inderal); ACE inhibitors (eg lisinopril); calcium antagonists (eg. nifedipine); angiotensin receptor antagonists (eg candesartan), α antagonists and diuretic agents (eg. furosemide, benzthiazide);
11) Haemostasis modulators such as, antithrombotics, activators of fibrinolysis and antiplatelet agents; thrombin antagonists; factor Xa inhibitors; factor VIIa inhibitors; antiplatelet agents (eg. aspirin, clopidogrel); anticoagulants (heparin and Low molecular weight analogues, hirudin) and warfarin;
12) Anti-inflammatory agents, such as non-steroidal anti-inflammatory drugs (eg. aspirin) and steroidal anti-inflammatory agents (eg. cortisone); and
13) Agents that prevent the reabsorption of glucose by the kidney (SGLT inhibitors).

EXAMPLES

The invention will now be illustrated by the following Examples in which, unless stated otherwise:
(i) temperatures are given in degrees Celsius (° C.); operations were carried out at room or ambient temperature, that is, at a temperature in the range of 18-25° C. and under an atmosphere of an inert gas such as argon;
(ii) evaporation of solvent was carried out using a rotary evaporator under reduced pressure (600-4000 Pa; 4.5-30 mmHg) with a bath temperature of up to 60° C.;
(iii) chromatography means flash chromatography on silica gel;
(iv) in general, the course of reactions was followed by TLC and reaction times are given for illustration only;
(v) yields are given for illustration only and are not necessarily those which can be obtained by diligent process development; preparations were repeated if more material was required;
(vi) where given, NMR data ($^1$H) is in the form of delta values for major diagnostic protons, given in parts per million (ppm) relative to tetramethylsilane (TMS), determined at 300 or 400 MHz (unless otherwise stated) using perdeuterio dimethyl sulfoxide (DMSO-$d_6$) as solvent, unless otherwise stated; peak multiplicities are shown thus: s, singlet; d, doublet; dd, doublet of doublets; dt, doublet of triplets; dm, doublet of multiplets; t, triplet, m, multiplet; br, broad;
(vii) chemical symbols have their usual meanings; SI units and symbols are used;
(viii) solvent ratios are given in volume:volume (v/v) terms;
(ix) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported;
(x) relative volume (rel vol) is the relative volume compared to the amount of the key intermediate. Relative volume is usually used to refer to the amount of solvent. For example if the key intermediate is 100 g and 1000 ml of solvent is used, then this is referred to as 10 rel vol of solvent;
(xi) The following abbreviations may be used below or in the process section hereinbefore:

| | |
|---|---|
| Et$_2$O | diethyl ether |
| DMF | dimethylformamide |
| DCM | dichloromethane |
| THF | tetrahydrofuran |
| DMSO | dimethylsulfoxide |
| EtOAc | ethyl acetate |
| MTBE | methyl tert-butyl ether |
| DSC | differential scanning calorimetry |

Reference Example 1

4-[4-(2-Adamantylcarbamoyl)-5-tert-butyl-pyrazol-1-yl]benzoic acid

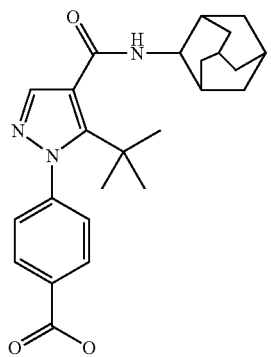

2M aqueous sodium hydroxide solution (51.7 mL, 103.32 mmol) was added to methyl 4-[4-(2-adamantylcarbamoyl)-5-tert-butyl-pyrazol-1-yl]benzoate (Intermediate #1) (4.5 g, 10.33 mmol) in methanol (100 mL). The mixture was stirred at 70° C. for 1 hour and then cooled to ambient temperature, concentrated under reduced pressure and diluted with water (100 mL). The reaction mixture was adjusted to pH 3 with 2M HCl. The reaction mixture was extracted with EtOAc (500 mL) and washed sequentially with water (2×100 mL), and saturated brine (50 mL). The organic layer was dried over MgSO4, filtered and evaporated to give a pale yellow solid. The solid was washed with EtOAc (20 mL), collected by filtration and dried under vacuum to give 4-[4-(2-adamantylcarbamoyl)-5-tert-butyl-pyrazol-1-yl]benzoic acid (3.89 g, 89%) as a cream crystalline solid.

1H NMR (400.13 MHz, DMSO-d$_6$) δ 1.19 (9H, s), 1.49 (2H, d), 1.70-1.96 (10H, m), 2.09 (2H, d), 3.98-4.01 (1H, m), 7.49-7.53 (2H, m), 7.61 (1H, s), 8.06-8.09 (2H, m), 8.20 (1H, d), 13.30 (1H, s)

m/z (ESI+) (M+H)+=422 m.p. 308.8° C. (onset)

Reference Example 1 may also be prepared as follows:
Aqueous sodium hydroxide (2M) (2.5 eq) was added portionwise over 5 minutes to a stirred suspension of methyl 4-[4-(2-adamantylcarbamoyl)-5-tert-butyl-pyrazol-1-yl] benzoate (Intermediate #1) (1.0 eq) in methanol (10 vol) at 20° C. (exotherm 20-27° C.). The resulting suspension was heated to 70° C. (jacket temperature), (batch refluxes approx 60-65° C.) for 1 hour (complete by LCMS). The orange reaction mixture was cooled to 20° C. (solution remained slightly cloudy) and filtered through celite to remove a small amount of solids. The filtrate was then poured into a flange flask and water (25 vol) was added. The mixture was then adjusted to pH 3 with 2M HCl (approx 800-850 ml) (turns very thick). The aqueous was then filtered and the pale yellow solid washed with water, sucked dry overnight, and washed with acetonitrile and finally 1:1 acetonitrile/diethyl ether and dried under vacuum at 50° C. for 72 hours (weekend) to give 4-[4-(2-adamantylcarbamoyl)-5-tertbutyl-pyrazol-1-yl]benzoic acid (80%) as a solid.

Intermediate #2: methyl 4-hydrazinylbenzoate hydrochloride

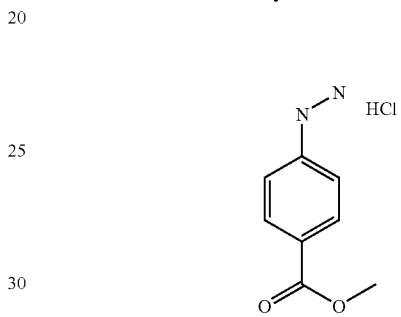

Hydrogen chloride 4M in Dioxan (100 mL, 399.60 mmol) was added to 4-Hydrazinobenzoic acid (15.2 g, 99.90 mmol) in MeOH (200 mL). The resulting suspension was stirred at 90° C. for 5 hours. After cooling to 20° C. the precipitate was collected by filtration, washed with Et2O (100 mL) and dried under vacuum to afford 2-(4-(methoxycarbonyl)phenyl)hydrazinium chloride (16.50 g, 82%) as a cream crystalline solid.

m/z (ESI−) (M−H)−=165; HPLC t$_R$=1.12 min

1H NMR (400.13 MHz, DMSO-d6) δ 3.81 (3H, s), 6.99-7.02 (2H, m), 7.86-7.90 (2H, m), 8.98 (1H, s), 10.47 (3H, s)

Intermediate # 2 may also be prepared as follows:
Methanolic hydrochloric acid solution (4M) (4 equiv., freshly prepared) was added to a suspension of 4-hydrazinobenzoic acid (1 equiv.) in methanol (12.6 vols.), under nitrogen.

The mixture was stirred under reflux for three hours and then cooled to below 15° C. The solid was collected by filtration, washed with MTBE (6.5 vols.) and dried in air to give the product as a solid.

TLC DCM:MeOH, 9:1, Product R$_f$ 0.87 mp 233.8-234.6° C.

Intermediate #3:
N-(2-adamantyl)-4,4-dimethyl-3-oxo-pentanamide

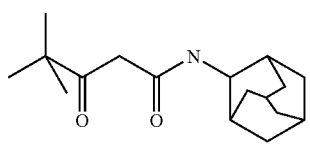

A 1M solution of solution of lithium bis(trimethylsilyl) amide in THF (22.84 ml, 22.84 mmol) was added to THF (25 mL) and cooled under nitrogen to −78° C. A solution of 3,3-dimethyl-2-butanone (2.287 g, 22.84 mmol) in THF (25 mL) was added drop wise over a period of 5 minutes. The resulting solution was stirred at −78° C. under nitrogen for 15 minutes. A solution of 2-isocyanatoadamantane (prepared from 2-adamantylamine hydrochloride by the method of R. Reck & C. Jochims *Chem. Ber.* 115 (1982) p 864) (3.68 g, 20.76 mmol) in THF (20 mL) was added over a period of 5 minutes. The resulting solution was stirred at −78° C. for 1 hour and then allowed to warm to 20° C. over 1 h. The reaction mixture was poured into saturated NH$_4$Cl (150 mL) and extracted with EtOAc (2×100 mL), the organic layer was washed with water (50 mL) and brine (50 mL) dried over MgSO4, filtered and evaporated to afford a yellow oil. The crude product was purified by flash silica chromatography, elution gradient 0 to 50% EtOAc in isohexane. Pure fractions were evaporated to dryness to afford N-(2-adamantyl)-4,4-dimethyl-3-oxo-pentanamide (4.64 g, 81%) as a white solid.

1H NMR (400.13 MHz, DMSO-d$_6$) δ 1.08-1.09 (9H, m), 1.50 (2H, d), 1.66-1.89 (10H, m), 1.95-2.00 (2H, m), 3.53 (1.4H, s), 3.80-3.94 (1H, m), 5.30 (0.3H, s), 7.77-7.87 (1H, m), 14.43 (0.3H, s) (2:1 mixture of keto and enol forms)

m/z (ESI+) (M+H)+=278

Intermediate #3 may also be prepared as follows:

Aqueous sodium hydroxide solution (3M) (5 vols.) was added to a stiffed suspension of 2-adamantylamine hydrochloride (1 equiv.) in water (5 vols.). DCM (5 vols.) was added to the resulting thick suspension and the phases separated. The aqueous was extracted with DCM (4×5 vols.) and the combined organics concentrated to give the free amine as a white solid.

Ethyl pivaloylacetate (1 equiv.) was added to a suspension of the free amine in xylenes (6.5 vols.), under nitrogen, and the mixture stiffed under reflux for 6.5 hours. The batch was cooled to room temperature and concentrated to dryness. The residue was purged with toluene (3×1 vol.) followed by hexane (3×1 vol.). The resulting solid was digested in hexane at 50° C. for five minutes and then cooled to room temperature. The white solid was filtered, washed with hexane (2 vols.) and dried in air.

TLC Hexane:EtOAc, 1:1, Product R$_f$ 0.66
mp 124.5-125.1° C.

Intermediate #4: (2)-N-(2-adamantyl)-2-(dimethylaminomethylidene)-4,4-dimethyl-3-oxo-pentanamide

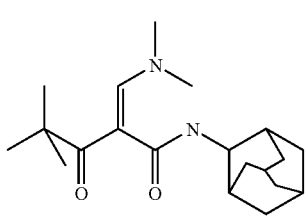

N,N-Dimethylformamide dimethyl acetal (3.02 mL, 22.71 mmol) was added to a stirred suspension of N-(2-adamantyl)-4,4-dimethyl-3-oxo-pentanamide (Intermediate #3) (5.25 g, 18.93 mmol) in 1,4-dioxane (50 mL) under nitrogen. The resulting mixture was stirred at 100° C. for 2 hours. The reaction mixture was evaporated to dryness and the resulting pale cream solid was dried under vacuum to afford (2)-N-(2-adamantyl)-2-(dimethylaminomethylidene)-4,4-dimethyl-3-oxo-pentanamide (5.83 g, 93%).

1H NMR (400.13 MHz, DMSO-d$_6$) δ 1.13 (9H, s), 1.47 (2H, d), 1.69-1.83 (10H, m), 2.03 (2H, d), 2.92 (6H, s), 3.90 (1H, d), 7.24 (1H, s), 7.94 (1H, d)

m/z (ESI+) (M+H)+=333

Intermediate #4 may also be prepared as follows:

N,N-Dimethylformamide dimethyl acetal (1.2 equivs.) was added to a solution of N-(2-adamantyl)-4,4-dimethyl-3-oxo-pentanamide (Intermediate #3) (1 equiv.) in 1,4-dioxane (9.6 vols.) under nitrogen. The mixture was heated under reflux for five hours and then cooled to room temperature. The solvent was removed in vacuo and the pale yellow solid used directly in the next stage.

TLC Hexane:EtOAc, 1:1, Product R$_f$ 0.94 (impurities: R$_f$ 0.06+0.66)
mp 143.6-147.6° C.

Intermediate #1: methyl 4-[4-(2-adamantylcarbamoyl)-5-tert-butyl-pyrazol-1-yl]benzoate

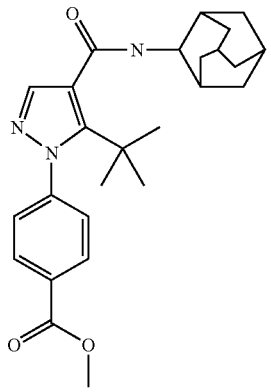

Methyl 4-hydrazinylbenzoate hydrochloride (Intermediate #2) (3.04 g, 15.00 mmol) was added in one portion to (2)-N-(2-adamantyl)-2-(dimethylaminomethylidene)-4,4-dimethyl-3-oxo-pentanamide (Intermediate #4) (4.99 g, 15 mmol) in ethanol (100 mL). 5 drops of acetic acid were added and the resulting solution was stirred at 80° C. for 2 hours. The reaction mixture was concentrated and diluted with EtOAc (500 mL), and washed sequentially with water (200 mL), and saturated brine (200 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford methyl 4-[4-(2-adamantylcarbamoyl)-5-tert-butyl-pyrazol-1-yl]benzoate (4.66 g, 71.3%) as a yellow solid.

1H NMR (400.13 MHz, DMSO-d$_6$) δ 1.19 (9H, s), 1.50 (2H, d), 1.69-1.95 (10H, m), 2.09 (2H, d), 3.91 (3H, s), 3.99 (1H, d), 7.53-7.56 (2H, m), 7.62 (1H, s), 8.09-8.12 (2H, m), 8.20 (1H, d)

m/z (ESI+) (M+H)+=436

Intermediate #1 may also be prepared as follows:

2-(4-(Methoxycarbonyl)phenyl)hydrazinium chloride (Intermediate #2) (1 equiv.) and then acetic acid (0.023 equivs.) were added to a solution of (2Z)—N-(2-adamantyl)-2-(dimethylamino-methylidene)-4,4-dimethyl-3-oxo-pentanamide (Intermediate #4) (1 equiv.) in methanol (200 vols.), under nitrogen. The mixture stirred under reflux for 1.5 hours, cooled, concentrated to below 3.5 vols. and the resulting suspension diluted with ethyl acetate (96 vols.). The suspension was washed with water (34.4 vols.) giving a solution which was washed with brine (34.4 vols.), dried (MgSO$_4$) and concentrated to dryness. The crude product was slurried in MTBE (9 vols.) and stirred for 15 minutes. The pale yellow solid was filtered, washed with MTBE (11.4 vols.) and dried under vacuum at 60° C.

TLC DCM:MeOH, 9:1, Product R$_f$ 0.86 (trace impurity R$_f$ 0.68)

mp 193.6-194.5° C.
4-[4-(2-Adamantylcarbamoyl)-5-tert-butyl-pyrazol-1-yl]benzoic acid may also be prepared as follows:

Hydrochloric acid (34.5% w/w, 15.88 g, 5.48 g @100.0%, 0.1504 mole, 1.0 mol. eq) and water (70 ml, 1.4 rel. vol) were added to a suspension of 4-hydrazinobenzoic acid (23.35 g, 22.88 g @100.0%, 0.1504 mole, 1.0 mol. eq) in methanol (1250 ml, 12.5 rel. vol). The resulting suspension was stirred for 30 min at 20 to 25° C. and a solution of N-(2-adamantyl)-2-(dimethylaminomethylidene)-4,4-dimethyl-3-oxo-pentanamide (intermediate #4) (53.47 g, 50.0 g @100.0%, 0.150 in 4 mole, 1.0 mol. eq) at 20-25° C. in methanol (250 ml, 5.0 rel. vol)] added over a period of 20 minutes followed by hydrochloric acid (34.5% w/w, 2.38 g, 0.82 g @100.0%, 0.02264 mole, 0.15 mol. eq) and water (70.0 ml, 1.4 rel. vol). The reaction mass temperature was increased to 62-65° C. and maintained for 90.0 min. For work up methanol solution was concentrated atmospherically until the residual volume 6.0 rel. vol (300.0 ml) remained. The resulting suspension was cooled to 20-25° C. and stirred for 1.0 hr. The product was filtered and washed with ethyl acetate (200.0 ml, 4.0 rel. vol) and sucked dry for 30 min. The product was dried under vacuum (100 mbar) at 50° C. for 8 hrs to give crude 4-[4-(2-adamantylcarbamoyl)-5-tert-butyl-pyrazol-1-yl]benzoic acid (47.0 g, 73.0%).

1H NMR (400.13 MHz, DMSO-d6) δ 1.19 (9H, s), 1.49 (2H, d), 1.70-1.96 (10H, m), 2.09 (2H, d), 3.98-4.01 (1H, m), 7.49-7.53 (2H, m), 7.61 (1H, s), 8.06-8.09 (2H, m), 8.20 (1H, d), 13.30 (1H, s)

m/z (ESI+) (M+H)+=422
m.p. 308.8° C. (onset)
Chromatographic Conditions: [HPLC]—
Zorbax SB-Aq, 150×4.6 mm, 5μ mobile phase used is formic acid buffer using acetonitrile as organic solvent, 1.0 mL/min flow rate, injection volume is 20 μL, run time is 18 mins using UV detector wavelength 220,320 nm
Retention Times [HPLC]
4-[4-(2-Adamantylcarbamoyl)-5-tert-butyl-pyrazol-1-yl]benzoic acid: (Relative retention time: 0.77 min)
(2)-N-(2-adamantyl)-2-(dimethylaminomethylidene)-4,4-dimethyl-3-oxo-pentanamide (Retention time: 14.2 min)

10.0% w/w Aqueous sodium hydroxide solution (109.1 g, 10.91 g @100.0%, 0.2727 mole, 1.15 mol. eq) was added to a suspension of crude 4-[4-(2-adamantylcarbamoyl)-5-tert-butyl-pyrazol-1-yl]benzoic acid (110.0 g, 100.0 g @100.0%, 0.2372 mole, 1.0 mol. eq) in water (1000.0 ml, 10.0 rel. vol) and stiffed for 15.0 min The un-dissolved product was filtered. To the resulting clear aqueous solution (filtrate), was added toluene (600.0 ml, 6.0 rel. vol) and stirred for 30.0 min. The reaction mass was settled for 1.0 hr for phase separation. The aqueous layer was separated and filtered through a Celite bed. To the aqueous layer was added methanol (300.0 ml, 3.0 rel. vol). The pH of the aqueous layer was slowly adjusted to 2.25 to 2.75 with dilute hydrochloric acid (3.8% w/w, 261.6 g, 9.94 @ 100.0%, 0.2727 mole, 1.15 mol. eq). The resulting suspension was stirred for 1.5 to 2.0 hrs and the product filtered and washed with 25.0% v/v methanol in water [500.0 ml, 5.0 rel. vol (125 ml methanol and 475 ml water mixture).

The product was dried under vacuum (100 mbar) at 50 to 60° C. for 16.0 hrs to provide 4-[4-(2-adamantylcarbamoyl)-5-tert-butyl-pyrazol-1-yl]benzoic acid (85.0 g, 85.0%) (form 1).

Intermediate #3

N-(2-Adamantyl)-4,4-dimethyl-3-oxo-pentanamide

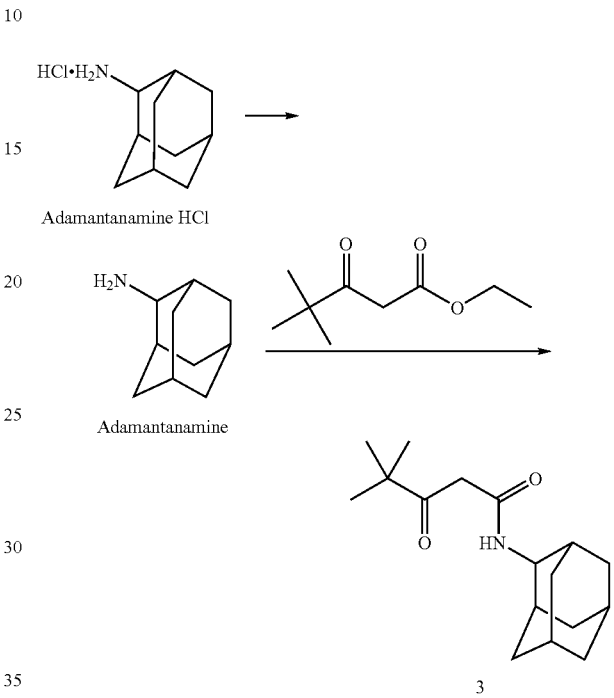

Intermediate #3 may also be prepared as follows: Toluene (400.0 ml, 4.0 rel. vol) was added to the solution of 2-adamantanamine hydrochloride (100.0 g, 98.0 g @ 100%, 0.5221 moles, 1.00 mol. eq) in water (500.0 ml, 5.0 rel. vol). 10.0% w/w Aqueous sodium hydroxide solution (261.02 g, 26.1 g @ 100.0%, 0.6526 moles, 1.25 mol. eq) was added to the above solution and stirred for 15 mins. The organic layer was separated from the aqueous and washed with 5.0% w/w sodium chloride solution (300.0 ml, 3.0 rel. vol). Ethyl pivaloylacetate (115.9 g, 0.6526 moles, 1.25 mol. eq) was added in one portion to the organic layer. The reaction mass was heated to reflux and toluene collected (550.0 ml, 5.5 rel. vol) azeotropically for 3 to 3.5 hrs, maintaining the temperature at 110° C. The reaction mass was cooled to 70-80° C. and n-heptane (1000.0 ml, 10.0 rel. vol) added over a period of 15 mins. It was further cooled to 25° C. and the resulting suspension was stirred for 1.0 hr. The suspended solid was collected by filtration, washed with n-heptane (400.0 ml, 4.0 rel. vol) and the product dried under vacuum (100 mbar) at 50-55° C. for 6.0 hrs to provide N-(2-adamantyl)-4,4-dimethyl-3-oxo-pentanamide 113.0 g, 75.8% as a white crystalline solid.

1H NMR (400.13 MHz, DMSO-d6) δ 1.08-1.09 (9H, m), 1.50 (2H, d), 1.66-1.89 (10H, m), 1.95-2.00 (2H, m), 3.53 (1.4H, s), 3.80-3.94 (1H, m), 5.30 (0.3H, s), 7.77-7.87 (1H, m), 14.43 (0.3H, s) (2:1 mixture of keto and enol forms)

m/z (ESI+) (M+H)+=278
Chromatographic Conditions:—(GC)
HP-5MS column, Helium as carrier gas, 1.0 mL/min flow rate, solvent delay up to 1.5 min, oven temperature=initial 50°

C., hold for 2 min, and then ramping @20° C./min up to 280° C. and injection volume is 1.0 μL.

Retention Times (GC)

2-Adamantanamine Hydrochloride (Retention time 8.1 min)

N-(2-adamantyl)-4,4-dimethyl-3-oxo-pentanamide (Relative retention time: 1.617 min)

Intermediate #4

(2)-N-(2-Adamantyl)-2-(dimethylaminomethylidene)-4,4-dimethyl-3-oxo-pentanamide

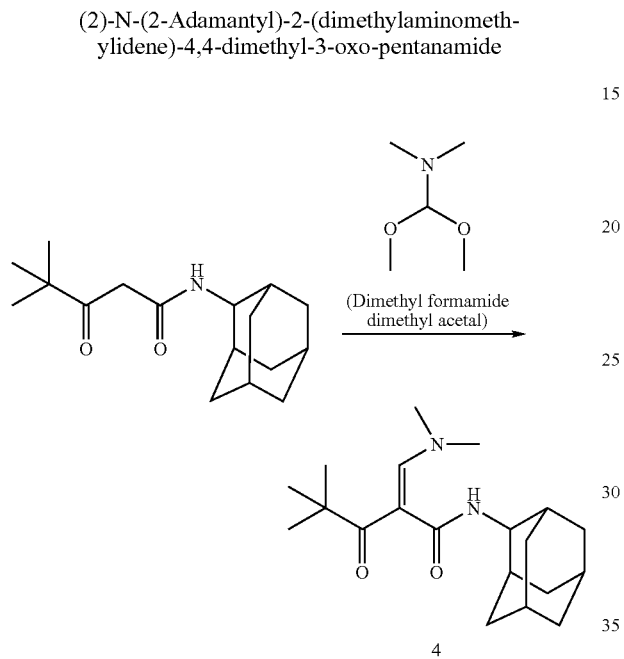

Intermediate #4 may also be prepared as follows: N,N-Dimethylformamide dimethyl acetal ((69.25 g, 63.02 g @100.0%, 0.5288 moles, 1.5 mol. eq) was added to a suspension of N-(2-adamantyl)-4,4-dimethyl-3-oxo-pentanamide (intermediate 3) (100 g, 97.8 g @ 100.0%, 0.3525 moles, 1.0 mol. eq) in n-heptane (800.0 ml, 8.20 rel. vol) and toluene (350.0 ml, 3.58 rel. vol). The reaction mass temperature was raised to 90-95° C. and maintained for 5.0 hrs then cooled to 80° C. and n-heptane (400.0 ml, 4.09 rel. vol) added. It was further cooled to 25° C. and the resulting suspension was collected by filtration, washed with n-heptane (400.0 ml, 4.09 rel. vol) and the product sucked dry for 30 min. The product was dried under vacuum (100 mbar) for 3.0 hrs at ambient temperature (20 to 25° C.) to provide (2)-N-(2-adamantyl)-2-(dimethylaminomethylidene)-4,4-dimethyl-3-oxo-pentanamide (100 g, 79.7%)

1H NMR (400.13 MHz, DMSO-d6) δ 1.13 (9H, s), 1.47 (2H, d), 1.69-1.83 (10H, m), 2.03 (2H, d), 2.92 (6H, s), 3.90 (1H, d), 7.24 (1H, s), 7.94 (1H, d)

m/z (ESI+) (M+H)+=333

Chromatographic Conditions: (HPLC)—

Sunfire C18, 150×4.6 mm, 5μ., mobile phase used is di-sodium hydrogen phosphate buffer using methanol as organic solvent, 1.0 mL/min flow rate, injection volume is 20 μL, run time is 20 mins using refractive index detector.

Retention Times (HPLC):

N-(2-Adamantyl)-4,4-dimethyl-3-oxo-pentanamide (Retention time: 11.0 min)

(2)-N-(2-adamantyl)-2-(dimethylaminomethylidene)-4,4-dimethyl-3-oxo-pentanamide (Relative retention time: 1.18 min)

Reference Example 2

Synthesis of (2)-N-(2-adamantyl)-2-(dimethylaminomethylidene)-4,4-dimethyl-3-oxo-pentanamide

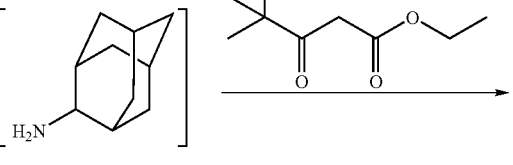
Adamine•HCl

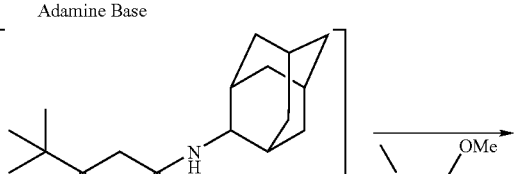
Adamine Base

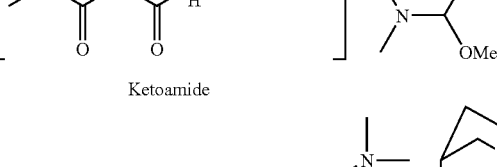
Ketoamide

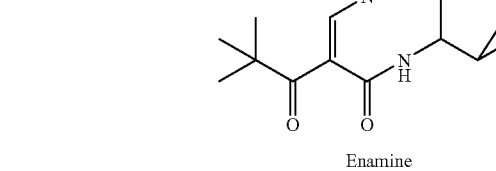
Enamine

To a suspension of 2-adamantanamine hydrochloride (25.0 g, 0.13 mol) in water (75.0 ml, 3.0 rel. vol) was added toluene (100.0 ml, 4.0 rel. vol). A 10.0% w/w aqueous sodium hydroxide solution (1.25 mol. eq) was fed into the above solution and stiffed for 10 to 15 minutes. The organic layer was separated and the aqueous layer re-extracted with toluene (75.0 ml, 3.0 rel. vol) and combined with the separated organic layer. The combined organic layer was washed with 5.0% w/w sodium chloride solution (75 ml, 3.0 rel. vol.) and separated. Ethyl pivaloylacetate (26.01 g, 0.15 mol) was added to the organic layer was the reaction mass heated to reflux at 110 to 112° C. The solvent (4 to 5 rel. vol.) was collected azeotropically over 4 to 5 hours. The reaction mass was cooled to 40 to 45° C. and n-heptane (200.0 ml, 8.0 rel. vol) added at 35 to 40° C. followed by DMF-DMA (26.45 g, 0.20 mol) and triethylamine (13.48 g, 0.13 mol) at 30 to 35° C. The reaction mass temperature was raised to 90 to 93° C. and maintained for 2 to 3 hours. The methanol generated as a by-product was collected azeotropically during the reaction. The reaction was cooled to 20 to 25° C. and stirred for 1.0 hr at that temperature. The precipitated product was filtered, bed washed with n-heptane (100.0 ml, 4.0 rel. vol) and the product dried under vacuum (50-100 mbar) at 35-40° C. for 3 to 4 hours to give (2)-N-(2-adamantyl)-2-(dimethylaminomethylidene)-4,4-dimethyl-3-oxo-pentanamide (Yield, 86%). The product was packed under nitrogen atmosphere and stored below 10° C. as it was found to be unstable at room temperature.

Alternatively (2)-N-(2-adamantyl)-2-(dimethylaminomethylidene)-4,4-dimethyl-3-oxo-pentanamide may be prepared as follows:

To a suspension of 2-adamantanamine hydrochloride (25.0 g, 0.13 mol) in water (75.0 ml, 3.0 rel. vol) was added toluene (100.0 ml, 4.0 rel. vol). A 10.0% w/w aqueous sodium hydroxide solution (1.25 mol. eq) was fed into the above solution and stirred for 10 to 15 minutes. The organic layer was separated and the aqueous layer re-extracted with toluene (75.0 ml, 3.0 rel. vol) and combined with the separated organic layer. The combined organic layer was washed with 5.0% w/w sodium chloride solution (75 ml, 3.0 rel. vol.) and separated. Ethyl pivaloylacetate (26.01 g, 0.15 mol) was added to the organic layer was the reaction mass heated to reflux at 110 to 112° C. The solvent (4 to 5 rel. vol.) was collected azeotropically over 4 to 5 hours. The reaction mass was cooled to 40 to 45° C. and n-heptane (200.0 ml, 8.0 rel. vol) added at 35 to 40° C. followed by DMF-DMA (26.45 g, 0.20 mol) at the same temperature. The reaction mass temperature was raised to 85 to 90° C. and maintained for 4 to 5 hours. The methanol generated as a by-product was collected azeotropically during the reaction. The reaction was cooled to 20 to 25° C. and stirred for 1.0 hr at that temperature. The precipitated product was filtered, bed washed with n-heptane (100.0 ml, 4.0 rel. vol) and the product dried under vacuum (50-100 mbar) at 35-40° C. for 3 to 4 hours to give (2)-N-(2-adamantyl)-2-(dimethylaminomethylidene)-4,4-dimethyl-3-oxo-pentanamide (Yield, 72%). The product was packed under nitrogen atmosphere and stored below 10° C. as it was found to be unstable at room temperature.

Chromatographic Conditions:—

Sunfire C18, 150×4.6 mm, 5µ., mobile phase used is disodium hydrogen phosphate buffer using methanol as organic solvent, 1.0 mL/min flow rate, injection volume is 20 µL, run time is 20 minutes using refractive index detector.

Retention Times:
  N-(2-adamantyl)-4,4-dimethyl-3-oxo-pentanamide RT: 11.0 min
  (2)-N-(2-adamantyl)-2-(dimethylaminomethylidene)-4,4-dimethyl-3-oxo-pentanamide RRT: 1.18 min
  1H NMR (400.13 MHz, DMSO-d6) δ 1.13 (9H, s), 1.47 (2H, d), 1.69-1.83 (10H, m), 2.03 (2H, d), 2.92 (6H, s), 3.90 (1H, d), 7.24 (1H, s), 7.94 (1H, d)
  m/z (ESI+) (M+H)+=333

If necessary the N-(2-adamantyl)-4,4-dimethyl-3-oxopentanamide intermediate may be isolated:

Chromatographic Conditions:—

HP-5MS column, Helium as carrier gas, 1.0 mL/min flow rate, solvent delay up to 1.5 min, oven temperature=initial 50° C., hold for 2 min, and then ramping @20° C./min up to 280° C. and injection volume is 1.0 µL.

Retention Times:
  2-Adamantanamine Hydrochloride RT 8.1 min
  N-(2-adamantyl)-4,4-dimethyl-3-oxo-pentanamide RRT: 1.617 min
  1H NMR (400.13 MHz, DMSO-d6) δ 1.08-1.09 (9H, m), 1.50 (2H, d), 1.66-1.89 (10H, m), 1.95-2.00 (2H, m), 3.53 (1.4H, s), 3.80-3.94 (1H, m), 5.30 (0.3H, s), 7.77-7.87 (1H, m), 14.43 (0.3H, s) (2:1 mixture of keto and enol forms)

m/z (ESI+) (M+H)+=278

Synthesis of 4-[4-(2-Adamantylcarbamoyl)-5-tert-butyl-pyrazol-1-yl]benzoic acid (Form-1)

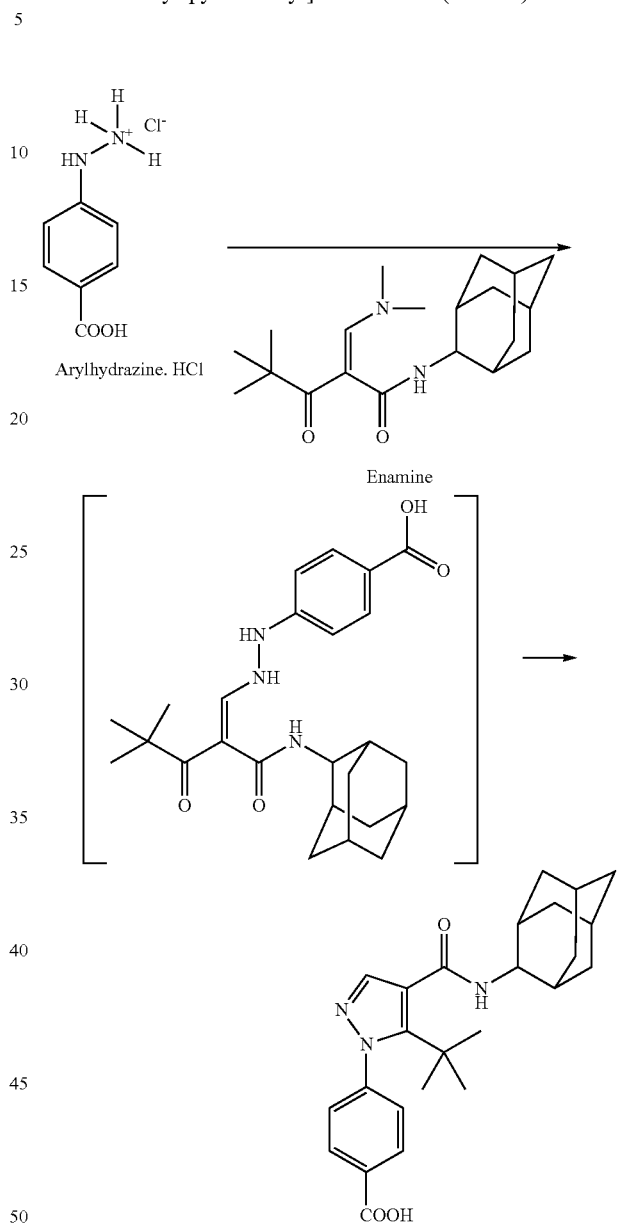

4-Hydrazinobenzoic acid.HCl (14.11 g, 0.075 mol), and (2)-N-(2-adamantyl)-2-(dimethylaminomethylidene)-4,4-dimethyl-3-oxo-pentanamide (25.0 g, 0.075 mol) were put into a jacketed reactor followed by isopropyl alcohol (315 ml, 12.6 rel. vol.) and water (35 ml, 1.4 rel. vol.). The reaction mass was stirred at 20 to 25° C. for about 45 to 60 minutes. The contents were heated to reflux at 78 to 80° C. and maintained at that temperature for 90 minutes. The reaction mass was cooled to 50 to 55° C. and then water (150 ml, 6 rel. vol.) added at the same temperature. The contents were further cooled to ambient temperature (20 to 25° C.) and stirred for 1.0 hour at the same temperature. The precipitated product was filtered and then washed with a mixture of 1:1 ratio of isopropyl alcohol:water (250 ml, 10.0 rel. vol.) to yield 4-[4-(2-adamantylcarbamoyl)-5-tert-butyl-pyrazol-1-yl]benzoic acid. The product was dried under vacuum at 50 to 55° C. for 4 to 5 hours and used without further purification (Yield: 80%).

1H NMR (400.13 MHz, DMSO-d6) δ 1.19 (9H, s), 1.49 (2H, d), 1.70-1.96 (10H, m), 2.09 (2H, d), 3.98-4.01 (1H, m), 7.49-7.53 (2H, m), 7.61 (1H, s), 8.06-8.09 (2H, m), 8.20 (1H, d), 13.30 (1H, s)

m/z (ESI+) (M+H)+=422 m.p. 308.8° C. (onset)

Chromatographic Conditions:—

Zorbax SB-Aq, 150×4.6 mm, 5μ. mobile phase used is formic acid buffer using acetonitrile as organic solvent, 1.0 mL/min flow rate, injection volume is 20 μL, run time is 18 minutes using UV detector wavelength 220,320 nm Retention Times:

[((2)-N-(2-Adamantyl)-2-(dimethylaminomethylidene)-4,4-dimethyl-3-oxo-pentanamide RT 14.2 min 4-[4-(2-Adamantylcarbamoyl)-5-tert-butyl-pyrazol-1-yl] benzoic acid RRT 0.77 min (10.0 min)

Intermediate RRT 0.79 (11.2 min)

Example 1

4-[4-(2-Adamantylcarbamoyl)-5-tert-butyl-pyrazol-1-yl]benzoic acid (Form 2)

Approximately 50 mg of 4-[4-(2-adamantylcarbamoyl)-5-tertbutyl-pyrazol-1-yl]benzoic acid as prepared above (Reference Example 1-Form 1) was placed in a vial with a magnetic flea, and approximately 2 ml of acetonitrile added. The vial was then sealed tightly with a cap. The slurry was then left to stir in a heated stirrer block with magnetic stirring capabilities at 50° C. After 3 days, the sample was removed from the plate, the cap taken off and the slurry left to dry under ambient conditions before it was analysed by XRPD and DSC. This form (Form 2) was determined to be crystalline by XRPD and seen to be different to the previous form. This material had a melting point of 310.9° C. (onset). It had 2 theta peaks measured using CuKa radiation at 18.0 and 17.7°. When the melting point was later measured using DSC, it was found to be 309.9° C.

Example 2

4-[4-(2-Adamantylcarbamoyl)-5-tert-butyl-pyrazol-1-yl]benzoic acid (Form 3)

Approximately 20 mg of 4-[4-(2-adamantylcarbamoyl)-5-tertbutyl-pyrazol-1-yl]benzoic acid (form 1) was placed in a vial with a magnetic flea, and approximately 2 ml of methanol added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form 3) was determined to be crystalline by XRPD and seen to be different to previously seen forms. This material had a melting point of 309.4° C. (onset). It had 2 theta peaks measured using CuKa radiation at 18.7 and 11.7°. When the melting point was later measured using DSC, it was found to be 309.3° C.

Example 3

4-[4-(2-Adamantylcarbamoyl)-5-tert-butyl-pyrazol-1-yl]benzoic acid (Form 4)

Approximately 20 mg of 4-[4-(2-adamantylcarbamoyl)-5-tertbutyl-pyrazol-1-yl]benzoic acid as Form 1 and 20 mg of the Form 3 material was placed in a vial with a magnetic flea, and approximately 2 ml of ethyl acetate added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form 4) was determined to be crystalline by XRPD and seen to be different to previously seen forms. This material (Form 4) had a melting point of 309.1° C. (onset).). It had 2 theta peaks measured using CuKa radiation at 16.2 and 20.6°. When the melting point was later measured using DSC, it was found to be 312.0° C.

Alternatively, acetonitrile may be used as the solvent at elevated temperature: Acetonitrile (800 ml, 8.0 rel. vol) was added to dry pure product ((4-[4-(2-Adamantylcarbamoyl)-5-tert-butyl-pyrazol-1-yl]benzoic acid form 1 (80.0 g) added and the slurry was heated to 75 to 78° C. The reaction was maintained at 75 to 78° C. for 72.0 hr, then cooled to 20 to 25° C. and stirred for 1.0 hr at 20 to 25° C. The product was filtered and sucked dry. It was then washed with acetonitrile (240.0 ml, 3.0 rel. vol) and sucked dried for 30.0 min The product was then dried under vacuum (100 mbar) at 50° C. for 16.0 hrs to give 4-[4-(2-Adamantylcarbamoyl)-5-tert-butyl-pyrazol-1-yl]benzoic acid Form-4 (72.0 g, 90.0%). Form-4 material (50 mg, 1% w/w, seed) was added to a suspension of (4-[4-(2-Adamantylcarbamoyl)-5-tert-butyl-pyrazol-1-yl] benzoic acid (form 1) 5.0 g in acetonitrile 50.0 ml and heated to 75-78° C. for 12 to 18 hrs. The reaction was cooled to 20 to 25° C. and stirred for 1.0 hr at 20 to 25° C. The product was filtered and sucked dry. It was then washed product with acetonitrile (15 ml) and sucked dry for 5-10.0 min The product was then dried under vacuum (100 mbar) at 50° C. for 16.0 hrs to give 4-[4-(2-adamantylcarbamoyl)-5-tert-butyl-pyrazol-1-yl]benzoic acid Form-4 (4.5 g, 89-90.0%). 4-[4-(2-Adamantylcarbamoyl)-5-tertbutyl-pyrazol-1-yl]benzoic acid as prepared above (Form 1) was suspended in acetonitrile (7 vol), seeded with 5 g of (form 4) and slurried at reflux for 3 days (jacket temperature 85° C.). A sample was taken and checked by DSC (shows 2 peaks). The sample was stirred at reflux for a further 3 days (weekend), cooled to 20° C., filtered, washed through with acetonitrile then diethyl ether, sucked dry and dried under vacuum at 50° C. for 48 hours to give a pale yellow solid (Form 4) (90%).

Alternatively:

Tetrahydrofuran (9.0 rel. vol) and water (0.5 rel vol) were added to 4-[4-(2-adamantylcarbamoyl)-5-tert-butyl-pyrazol-1-yl]benzoic acid form 1 (20.0 g, 0.047 mol) and the mixture stirred for 15 minutes and then filtered through filter paper. The residue was washed with tetrahydrofuran (1.0 rel. vol) and the combined filtrate transferred to a reactor and the reaction temperature raised to 58 to 62° C. Acetonitrile (20.0 rel. vol) was added whilst maintaining the reaction at 55 to 65° C. The reaction temperature was raised to 68±2° C., maintained there for 22 hours, then cooled to 20 to 25° C. and stirred for 2 hours. The product was filtered and the bed washed with acetonitrile (5.0 rel. vol). The wet cake was dried under vacuum (50-100 mbar) at 45 to 50° C. for 4 hours to give polymorph 4 (yield 80%) as confirmed by XRPD.

Alternatively:

Tetrahydrofuran (10.0 rel. vol) was added to 4-[4-(2-adamantylcarbamoyl)-5-tert-butyl-pyrazol-1-yl]benzoic acid form 1 (5.0 g, 0.012 mol) and the temperature raised to 58 to 62° C. Acetonitrile (20.0 rel. vol) was added whilst maintaining the reaction at 55 to 65° C. The temperature of the reaction was maintained at 68±2° C. for 20 hours. The contents were cooled to 20 to 25° C. and stiffed for 2 hours. The product was filtered and the wet cake washed with acetonitrile (5.0 vol)

and then dried in a vacuum oven (50-100 mbar) at 45 to 50° C. for 4 hours to give polymorph 4 (yield 90%) as confirmed by XRPD and Solid state NMR.

Alternatively:

N,N-Dimethylformamide (5.0 rel. vol) and acetonitrile (5.0 vol) were added to 4-[4-(2-adamantylcarbamoyl)-5-tert-butyl-pyrazol-1-yl]benzoic acid form 1 (5.0 g, 0.012 mol) and the reaction temperature raised to 60 to 65° C. Acetonitrile (15.0 rel. vol) was added whilst maintaining the temperature at 55 to 65° C. The temperature of the reaction was raised to 75 to 78° C. and maintained there for 20 hours. The contents were cooled to 20 to 25° C. and stirred for 2 hours. The product was filtered and bed washed with acetonitrile (5.0 rel. vol) and then dried in a vacuum oven (50-100 mbar) at 45 to 50° C. for 4 hours to give polymorph 4 (yield 88%) as confirmed by XRPD.

Alternatively:

Acetic acid (10.0 rel. vol) was added to 4-[4-(2-adamantylcarbamoyl)-5-tert-butyl-pyrazol-1-yl]benzoic acid form 1 (5.0 g, 0.012 mol) and the temperature raised to 75 to 78° C. Acetonitrile (20.0 rel. vol) was added whilst maintaining the temperature at 70 to 78° C. The mixture was stirred at 75 to 78° C. and maintained there for 22 hours. The contents were cooled to 20 to 25° C. and stiffed for 2 hours. The product was filtered and the bed washed with acetonitrile (5.0 rel. vol) and then dried in a vacuum oven (50-100 mbar) at 45 to 50° C. for 4 hours to polymorph 4 (yield 66%) as confirmed by XRPD.

Alternatively:

2-Methyl-THF (10.0 rel. vol) was added to 4-[4-(2-adamantylcarbamoyl)-5-tert-butyl-pyrazol-1-yl]benzoic acid form 1 (5.0 g, 0.012 mol) and the temperature raised to 70 to 75° C. Acetonitrile (20.0 rel. vol) was added whilst maintaining the temperature at 70 to 75° C. and then allowed to stir at 75 to 78° C. for 23 hours. The contents were cooled to 20 to 25° C. and stirred for 2 hours. The product was filtered and the bed washed with acetonitrile (5.0 rel. vol) and then dried in a vacuum oven (50-100 mbar) at 45 to 50° C. for 4 hours to give polymorph 4 (yield 93%) as confirmed by XRPD.

Alternatively:

4-[4-(2-Adamantylcarbamoyl)-5-tert-butyl-pyrazol-1-yl]benzoic acid (form 1—prepared as in reference example 2) (20.0 g, 0.047 mol) followed by tetrahydrofuran (9.0 rel. vol) and water (0.5 rel vol) were added to a suitable jacketed reactor. The contents were stirred for 15 minutes, filtered through filter paper and washed with tetrahydrofuran (1.0 rel. vol). The combined filtrate was transferred to reactor and temperature of mass increased to 58 to 62° C. Acetonitrile (20.0 rel. vol) was added whilst maintaining the temperature at 55 to 65° C. The temperature of reaction mass was increased to 68±2° C. and maintained there for 22 hours. The contents were cooled to 20 to 25° C. and stirred for 2 hours. The product was filtered and the bed washed with acetonitrile (5.0 rel. vol). The wet cake was dried under vacuum (50-100 mbar) at 45 to 50° C. for 4 hours to yield polymorph form 4 (80%).

The invention claimed is:

1. A crystalline form of 4-[4-(2-adamantylcarbamoyl)-5-tert-butyl-pyrazol-1-yl]benzoic acid having an X-ray powder diffraction pattern with peaks at the following 2-theta values measured using CuKa radiation: 18.0, 17.7, 18.4, 8.9, 20.5, 10.4, 21.9, 13.4, 27.6 and 16.7°.

2. A crystalline form of 4-[4-(2-adamantylcarbamoyl)-5-tert-butyl-pyrazol-1-yl]benzoic acid having an X-ray diffraction pattern, using CuKa radiation, substantially the same as shown in FIG. 1.

3. A crystalline form of 4-[4-(2-adamantylcarbamoyl)-5-tert-butyl-pyrazol-1-yl]benzoic acid having an X-ray powder diffraction pattern with specific peaks, measured using CuKa radiation, at 2-theta values of about 18.0, 17.7, 18.4, 8.9, 20.5, 10.4, 21.9, 13.4, 27.6 and 16.7°.

4. A crystalline form of 4-[4-(2-adamantylcarbamoyl)-5-tert-butyl-pyrazol-1-yl]benzoic acid having an X-ray powder diffraction pattern with specific peaks, measured using CuKa radiation, at 2-theta values of 18.0, 17.7, 18.4, 8.9, 20.5, 10.4, 21.9, 13.4, 27.6 and 16.7°, wherein said values may be plus or minus 0.5° 2-theta.

5. A crystalline form of 4-[4-(2-adamantylcarbamoyl)-5-tert-butyl-pyrazol-1-yl]benzoic acid having an X-ray powder diffraction pattern with specific peaks, measured using CuKa radiation, at 2-theta values of 18.0, 17.7, 18.4, 8.9, 20.5, 10.4, 21.9, 13.4, 27.6 and 16.7°, wherein said values may be plus or minus 0.2° 2-theta.

6. A method of producing a 11βHSD1 inhibitory effect by administering an effective amount of a compound according to any one of claims 1, 2 and 3 to 5 to a mammal in need of such treatment.

7. A method according to claim 6 wherein the 11βHSD1 inhibitory effect is to treat type 2 diabetes.

* * * * *